United States Patent
Wang et al.

(10) Patent No.: US 10,052,372 B2
(45) Date of Patent: Aug. 21, 2018

(54) T CELL EXPANSION

(71) Applicant: Tessa Therapeutics Pte Ltd, Singapore (SG)

(72) Inventors: Peter Wang, Singapore (SG); Chunxiao Wu, Singapore (SG)

(73) Assignee: TESSA THERAPEUTICS PTE LTD, Singapore (SG)

( * ) Notice: Subject to any disclaimer, the term of this patent is extended or adjusted under 35 U.S.C. 154(b) by 214 days.

(21) Appl. No.: 15/290,230

(22) Filed: Oct. 11, 2016

(65) Prior Publication Data

US 2017/0028042 A1 Feb. 2, 2017

Related U.S. Application Data

(60) Provisional application No. 62/340,605, filed on May 24, 2016.

(51) Int. Cl.
| | |
|---|---|
| *A61K 39/12* | (2006.01) |
| *A61K 35/17* | (2015.01) |
| *A61K 39/00* | (2006.01) |
| *C12N 5/0783* | (2010.01) |

(52) U.S. Cl.
CPC .......... *A61K 39/0011* (2013.01); *A61K 35/17* (2013.01); *A61K 39/12* (2013.01); *C12N 5/0638* (2013.01); *A61K 2039/5154* (2013.01); *A61K 2039/5158* (2013.01); *C12N 2500/32* (2013.01); *C12N 2501/2302* (2013.01); *C12N 2502/11* (2013.01); *C12N 2502/1107* (2013.01); *C12N 2502/99* (2013.01); *C12N 2710/16034* (2013.01)

(58) Field of Classification Search
None
See application file for complete search history.

(56) References Cited

U.S. PATENT DOCUMENTS

| | | | | |
|---|---|---|---|---|
| 5,962,318 | A * | 10/1999 | Rooney | A61K 39/0011 424/93.1 |
| 7,883,889 | B2 * | 2/2011 | De Santis | A61K 39/0011 424/93.21 |
| 8,809,050 | B2 * | 8/2014 | Vera | C12N 5/0636 435/325 |
| 2015/0017723 | A1 * | 1/2015 | Rooney | A61K 35/17 435/377 |

FOREIGN PATENT DOCUMENTS

WO WO 99/25812 5/1999

OTHER PUBLICATIONS

Smith C, Økern G, Rehan S, Beagley L, Lee SK, Aarvak T, Schjetne KW, Khanna R. Ex vivo expansion of human T cells for adoptive immunotherapy using the novel Xeno-free CTS Immune Cell Serum Replacement. Clin Transl Immunology. Jan. 16, 2015;4(1):e31.*

Bollard et al., "Cytotoxic T Lymphocyte Therapy for Epstein-Barr Virus Hodgkin's Disease", J. Exp. Med. vol. 200, No. 12, Dec. 20, 2004, 1623-1633.

Chia et al., "Adoptive T-cell Transfer and Chemotherapy in the First-line Treatment of Metastatic and/or Locally Recurrent Nasopharyngeal Carcinoma", www.moleculartherapy.org, vol. 22, No. 1, 132-139.

Hussain et al., "Lymphoblastoid Cell lines: a Continuous in Vitro Source of Cells to Study Carcinogen Sensitivity and DNA Repair", IJMCM Spring 2012, vol. 1, No. 2, 75-87.

Louis et al., "Adoptive Transfer of EBV-specific T Cells Results in Sustained Clinical Responses in Patients With Locoregional Nasopharyngeal Carcinoma", J. Immunother, vol. 33, No. 9, Nov.-Dec. 2010, 983-990

Rooney et al., "Infusion of Cytotoxic T Cells for the Prevention and Treatment of Epstein-Barr Virus-Induced Lymphoma in Allogeneic Transplant Recipients", Blood, (Sep. 1, 1998), vol. 92, No. 5, 1549-1555.

Smith et al., "Production of Genetically Modified Epstein-Barr Virus-Specific Cytotoxic T Cells for Adoptive Transfer to Patients at High Risk of EBV-Associated Lymphoproliferative Disease", Journal of Hematotherapy, 4:73-79 (1995).

Staathof et al., "Treatment of nasopharyngeal carcinoma with Epstein-Barr virus-specific T lymphocytes", Blood, Mar. 1, 2005, vol. 105, No. 5:1898-1904.

Borysiewicz et al., "Human cytomegalovirus-specific cytotoxic T cells: their precursor frequency and stage specificity", Eur. J. Immunol. 1988, 18:269-275.

International Search Report and Written Opinion for PCT/EP2016/075644, dated Jan. 10, 2017, 14 pages.

Lalvani et al., "Optimization of a peptide-based protocol employing IL-7 for in vitro restimulation of human cytotoxic T lymphocyte precursors", Journal of Immunological Methods 210 (1997) 65-77.

Munn et al., "Inhibition of T Cell Proliferation by Macrophage Tryptophan Catabolism", J. Exp. Med., vol. 189, No. 9, May 3, 1999, 1363-1372.

Redchenko et al., "Accessing Epstein-Barr Virus-Specific T-Cell Memory with Peptide-Loaded Dendritic Cells", Journal of Virology, Jan. 1999, vol. 73, No. 1, p. 334-342.

* cited by examiner

*Primary Examiner* — Benjamin P Blumel
(74) *Attorney, Agent, or Firm* — Swanson & Bratschun, L.L.C.

(57) ABSTRACT

A method of treating a cancer in a subject is disclosed, comprising: (1) isolating T cells from a subject; generating or expanding a population of T cells specific for a virus by a method comprising: stimulating T cells by culture in the presence of antigen presenting cells (APCs) presenting a peptide of the virus, wherein 10 to 25% of the media in which the cells are cultured is conditioned media obtained from a stimulation culture comprising T cells and APCs presenting a peptide of the virus; and (3) administering the generated or expanded population of T cells to a subject. Also disclosed are methods for generating or expanding a population of T cells specific for a virus.

18 Claims, 3 Drawing Sheets

T CELL EXPANSION

FIELD OF THE INVENTION

The present invention relates to methods for generating and/or expanding populations of virus-specific T cells.

BACKGROUND TO THE INVENTION

Adoptive transfer of virus-specific T cells is a promising strategy for the prevention and treatment of viral disease.

Adoptive transfer requires the use of a large number of T cells. For example, Chia et al., Mol Ther (2014) 22(1): 132-139 describe treatment of EBV-positive nasopharyngeal carcinoma (NPC) by adoptive transfer of a median total number of $9.6 \times 10^8$ EBV-CTLs (ranging from 6.3 to $10.3 \times 10^8$ CTLs).

A major problem for therapy by adoptive T cell transfer is the period of time taken to generate sufficiently large numbers of virus-specific T cells for administration. Chia et al. (supra) reported that the median time taken to produce and the first dose of CTLs was 13 weeks (ranging from 8 to 22 weeks). Moreover, it is reported that in this study that for 3 patients there was deviation from the scheduled therapy due to delays in CTL production.

SUMMARY OF THE INVENTION

Methods for generating and/or expanding populations of virus-specific T cells typically include several rounds of stimulation of T cells with antigen presenting cells presenting peptide of the virus of interest (i.e. the virus for which the T cells are specific).

The present invention is based on the finding that populations of virus-specific T cells can be expanded more rapidly by performing re-stimulations in the presence of conditioned media obtained from a stimulation step. Advantageously, large numbers of virus-specific T cells can thereby be obtained in a shorter period of time as compared to prior art methods. The present invention is therefore useful for generating/expanding populations of virus-specific T cells for use in research and/or therapeutic applications.

In one aspect, the present invention provides a method for generating or expanding a population of T cells specific for a virus, comprising stimulating T cells by culture in the presence of antigen presenting cells (APCs) presenting a peptide of the virus, wherein at least 10% of the media in which the cells are cultured is conditioned media obtained from a stimulation culture comprising T cells and APCs presenting a peptide of the virus.

In another aspect, the present invention provides a method for accelerating the rate of expansion of a virus-specific T cell population, the method comprising stimulating T cells by culture in the presence of antigen presenting cells (APCs) presenting a peptide of the virus, wherein at least 10% of the media in which the cells are cultured is conditioned media obtained from a stimulation culture comprising T cells and APCs presenting a peptide of the virus.

In another aspect, the present invention provides a method for generating or expanding a population of T cells specific for a virus, comprising:
  (i) stimulating T cells by culture in the presence of antigen presenting cells (APCs) presenting a peptide of the virus; and
  (ii) re-stimulating the T cells by culture in the presence of APCs presenting a peptide of the virus, wherein at least 10% of the media in which the cells are cultured is conditioned media obtained from a stimulation culture of T cells and APCs presenting a peptide of the virus.

In another aspect, the present invention provides a method for generating or expanding a population of T cells specific for a virus, wherein the method comprises:
  (i) stimulating T cells by culture in the presence of antigen presenting cells (APCs) presenting a peptide of the virus;
  (ii) re-stimulating the T cells by culture in the presence of APCs presenting a peptide of the virus; and
  (iii) re-stimulating the T cells by culture in the presence of APCs presenting a peptide of the virus, wherein at least 10% of the media in which the cells are cultured is conditioned media obtained from a stimulation culture of T cells and APCs presenting a peptide of the virus. In some embodiments of the method the conditioned media is obtained from the stimulation culture of step (ii).

In another aspect, the present invention provides a method for generating or expanding a population of T cells specific for a virus, comprising:
  (i) stimulating T cells by culture in the presence of antigen presenting cells (APCs) presenting a peptide of the virus;
  (ii) collecting the cells obtained by step (i), and;
  (iii) re-stimulating the T cells by culture in the presence of APCs presenting a peptide of the virus, wherein at least 10% of the media in which the cells are cultured is conditioned media obtained from a stimulation culture of T cells and APCs presenting a peptide of the virus.

In another aspect, the present invention provides a method for generating or expanding a population of T cells specific for a virus, wherein the method comprises:
  (i) stimulating T cells by culture in the presence of antigen presenting cells (APCs) presenting a peptide of the virus;
  (ii) collecting the cells obtained by step (i);
  (iii) re-stimulating the T cells by culture in the presence of APCs presenting a peptide of the virus;
  (iv) collecting the cells obtained by step (iii); and
  (v) re-stimulating the T cells by culture in the presence of APCs presenting a peptide of the virus, wherein at least 10% of the media in which the cells are cultured is conditioned media obtained from a stimulation culture of T cells and APCs presenting a peptide of the virus. In some embodiments of the method the conditioned media is obtained from the stimulation culture of step (iii).

In connection with the various aspects of the present invention, in some embodiments the conditioned media is obtained from a stimulation culture of T cells and APCs presenting a peptide of the virus after a culture period of 1 to 8 days. In some embodiments, the conditioned media is obtained from a stimulation culture of T cells and APCs at a responder:stimulator ratio of 1:1 to 10:1. In some embodiments, the APCs presenting a peptide of the virus are EBV-transformed lymphoblastoid cell line (LCL) cells. In some embodiments, the at least 10% of conditioned media is 20 to 40% of conditioned media. In some embodiments, the at least 10% of conditioned media is 10 to 25%, preferably about 15% of conditioned media.

In another aspect, the present invention provides a method for generating or expanding a population of Epstein-Barr Virus (EBV)-specific T cells, comprising stimulating T cells by culture in the presence of EBV-transformed LCLs at a responder to stimulator ratio of 2:1 to 7:1 for a period of 1 to 8 days, in media comprising:
- (a) cell culture media comprising 40-50% RPMI-1640 medium, 40-50% Click's medium, 5-20% FBS, and 1-5 mM L-glutamine,
- (b) at least 10% conditioned media obtained by a method comprising: stimulating T cells by culture in the presence of EBV-transformed LCLs at a responder to stimulator ratio of 2:1 to 7:1 in cell culture media comprising 40-50% RPMI-1640 medium, 40-50% Click's medium, 5-20% FBS, and 1-5 mM L-glutamine, and added IL-2 at a final concentration of 10-200 IU/ml, for a period of 1 to 8 days, and
- (c) added IL-2 at a final concentration of 10-200 IU/ml.

In another aspect, the present invention provides a method for accelerating the rate of expansion of a population of Epstein-Barr Virus (EBV)-specific T cells, comprising stimulating T cells by culture in the presence of EBV-transformed LCLs at a responder to stimulator ratio of 2:1 to 7:1 for a period of 1 to 8 days, in media comprising:
- (a) cell culture media comprising 40-50% RPMI-1640 medium, 40-50% Click's medium, 5-20% FBS, and 1-5 mM L-glutamine,
- (b) at least 10% conditioned media obtained by a method comprising: stimulating T cells by culture in the presence of EBV-transformed LCLs at a responder to stimulator ratio of 2:1 to 7:1 in cell culture media comprising 40-50% RPMI-1640 medium, 40-50% Click's medium, 5-20% FBS, and 1-5 mM L-glutamine, and added IL-2 at a final concentration of 10-200 IU/ml, for a period of 1 to 8 days, and
- (c) added IL-2 at a final concentration of 10-200 IU/ml.

In another aspect, the present invention provides a method for generating or expanding a population of Epstein-Barr Virus (EBV)-specific T cells, comprising:
- (i) stimulating T cells by culturing PBMCs in the presence of EBV-transformed LCLs at a responder to stimulator ratio of 10:1 to 80:1 in cell culture media comprising 40-50% RPMI-1640 medium, 40-50% Click's medium, 5-20% FBS, and 1-5 mM L-glutamine for a period of 7 to 14 days;
- (ii) collecting the cells obtained by step (i);
- (iii) re-stimulating the T cells by culturing cells collected at step (ii) in the presence of EBV-transformed LCLs at a responder to stimulator ratio of 2:1 to 7:1 in cell culture media comprising 40-50% RPMI-1640 medium, 40-50% Click's medium, 5-20% FBS, and 1-5 mM L-glutamine, and added IL-2 at a final concentration of 10-200 IU/ml, for a period of 1 to 8 days;
- (iv) collecting the cells obtained by step (iii), and;
- (v) re-stimulating the T cells by culturing cells collected at step (iv) in the presence of EBV-transformed at a responder to stimulator ratio of 2:1 to 7:1 for a period of 1 to 8 days in media comprising: (a) cell culture media comprising 40-50% RPMI-1640 medium, 40-50% Click's medium, 5-20% FBS, and 1-5 mM L-glutamine, (b) at least 10% conditioned media obtained at the end point of step (iii), and (c) added IL-2 at a final concentration of 10-200 (e.g. 40-100) IU/ml.

In some embodiments, the method additionally comprises:
- (vi) collecting the cells obtained by step (v), and;
- (vii) re-stimulating the T cells by culturing cells collected at step (vi) in the presence of EBV-transformed LCLs at a responder to stimulator ratio of 2:1 to 7:1 for a period of 1 to 8 days in media comprising: (a) cell culture media comprising 40-50% RPMI-1640 medium, 40-50% Click's medium, 5-20% FBS, and 1-5 mM L-glutamine, (b) at least 10% conditioned media obtained at the end point of step (v), and (c) added IL-2 at a final concentration of 10-200 (e.g. 40-100) IU/ml.

In some embodiments, the method comprises additional steps of collecting cells, and re-stimulating the T cells by culturing the collected cells in the presence of EBV-transformed LCLs (e.g. irradiated, EBV-transformed LCLs) at a responder to stimulator ratio of 2:1 to 7:1 for a period of 1 to 8 days in media comprising:
- (a) cell culture media comprising 40-50% RPMI-1640 medium, 40-50% Click's medium, 5-20% FBS, and 1-5 mM L-glutamine, (b) at least 10% conditioned media obtained at the end point of the preceding stimulation step, and (c) added IL-2 at a final concentration of 10-200 IU/ml.

In another aspect, the present invention provides a method of treating a cancer in a subject, the method comprising:
- (1) isolating T cells from a subject;
- (2) generating or expanding a population of T cells specific for a virus by a method comprising: stimulating T cells by culture in the presence of antigen presenting cells (APCs) presenting a peptide of the virus, wherein 10 to 25% of the media in which the cells are cultured is conditioned media obtained from a stimulation culture comprising T cells and APCs presenting a peptide of the virus; and
- (3) administering the generated or expanded population of T cells to a subject.

In some embodiments, the conditioned media is obtained from a stimulation culture comprising T cells and APCs presenting a peptide of the virus at a responder:stimulator ratio of 2:1 to 7:1 for a period of 1 to 8 days. In some embodiments, stimulating T cells by culture in the presence of APCs presenting a peptide of the virus comprises culture in the presence of EBV-transformed LCLs at a responder to stimulator ratio of 2:1 to 7:1 for a period of 1 to 8 days, in media comprising: (a) cell culture media comprising 40-50% RPMI-1640 medium, 40-50% Click's medium, 5-20% FBS, and 1-5 mM L-glutamine, (b) 10% to 25% conditioned media obtained by a method comprising: stimulating T cells by culture in the presence of EBV-transformed LCLs at a responder to stimulator ratio of 2:1 to 7:1 in cell culture media comprising 40-50% RPMI-1640 medium, 40-50% Click's medium, 5-20% FBS, and 1-5 mM L-glutamine, and added IL-2 at a final concentration of 10-200 IU/ml, for a period of 1 to 8 days, and (c) added IL-2 at a final concentration of 10-200 IU/ml. In some embodiments, the APCs presenting a peptide of the virus are EBV-transformed lymphoblastoid cell line (LCL) cells. In some embodiments, the cancer is an EBV-positive cancer. In some embodiments, the cancer is EBV-positive nasopharyngeal carcinoma (NPC). In some embodiments, about 15% of the media in which the cells are cultured is conditioned media. In some embodiments, step (2) additionally comprises: collecting the generated or expanded population of T cells.

In another aspect, the present invention provides a method of treating a cancer in a subject, the method comprising:
- (1) isolating T cells from a subject;
- (2) generating or expanding a population of T cells specific for a virus by a method comprising: stimulating T cells by culture in the presence of antigen presenting cells (APCs) presenting a peptide of the virus, wherein 10 to 25% of the media in which the cells are cultured is conditioned media, wherein the conditioned media is obtained from a stimulation culture comprising T cells and APCs presenting a peptide of the virus at a responder:stimulator ratio of 2:1 to 7:1 for a period of 1 to 8 days; and (3) administering the generated or expanded population of T cells to a subject.

In some embodiments, stimulating T cells by culture in the presence of APCs presenting a peptide of the virus comprises culture in the presence of EBV-transformed LCLs at a responder to stimulator ratio of 2:1 to 7:1 for a period of 1 to 8 days, in media comprising: (a) cell culture media comprising 40-50% RPMI-1640 medium, 40-50% Click's medium, 5-20% FBS, and 1-5 mM L-glutamine, (b) 10% to 25% conditioned media obtained by a method comprising: stimulating T cells by culture in the presence of EBV-transformed LCLs at a responder to stimulator ratio of 2:1 to 7:1 in cell culture media comprising 40-50% RPMI-1640 medium, 40-50% Click's medium, 5-20% FBS, and 1-5 mM L-glutamine, and added IL-2 at a final concentration of 10-200 IU/ml, for a period of 1 to 8 days, and (c) added IL-2 at a final concentration of 10-200 IU/ml. In some embodiments, the cancer is an EBV-positive cancer. In some embodiments, the cancer is EBV-positive nasopharyngeal carcinoma (NPC). In some embodiments, about 15% of the media in which the cells are cultured is conditioned media. In some embodiments, step (2) additionally comprises: collecting the generated or expanded population of T cells.

In another aspect, the present invention provides a method for generating or expanding a population of T cells specific for a virus, comprising stimulating T cells by culture in the presence of antigen presenting cells (APCs) presenting a peptide of the virus, wherein 10% to 25% of the media in which the cells are cultured is conditioned media obtained from a stimulation culture comprising T cells and APCs presenting a peptide of the virus.

In some embodiments, the conditioned media is obtained from a stimulation culture comprising T cells and APCs presenting a peptide of the virus at a responder:stimulator ratio of 2:1 to 7:1 for a period of 1 to 8 days. In some embodiments, stimulating T cells by culture in the presence of APCs presenting a peptide of the virus comprises culture in the presence of EBV-transformed LCLs at a responder to stimulator ratio of 2:1 to 7:1 for a period of 1 to 8 days, in media comprising: (a) cell culture media comprising 40-50% RPMI-1640 medium, 40-50% Click's medium, 5-20% FBS, and 1-5 mM L-glutamine, (b) 10% to 25% conditioned media obtained by a method comprising: stimulating T cells by culture in the presence of EBV-transformed LCLs at a responder to stimulator ratio of 2:1 to 7:1 in cell culture media comprising 40-50% RPMI-1640 medium, 40-50% Click's medium, 5-20% FBS, and 1-5 mM L-glutamine, and added IL-2 at a final concentration of 10-200 IU/ml, for a period of 1 to 8 days, and (c) added IL-2 at a final concentration of 10-200 IU/ml. In some embodiments, the APCs presenting a peptide of the virus are EBV-transformed lymphoblastoid cell line (LCL) cells. In some embodiments, the 10% to 25% of conditioned media is about 15% of conditioned media. In some embodiments, step (2) additionally comprises: collecting the generated or expanded population of T cells.

DESCRIPTION

T Cells and Antigen Presenting Cells

The present invention is concerned with the generation and/or expansion of populations of virus-specific T cells.

As used herein, a virus-specific T cell is a T cell reactive to cells infected with, or comprising a peptide of, a virus. A virus-specific T cell comprises a T Cell Receptor (TCR) capable of binding to an MHC molecule presenting a peptide of the virus for which the T cell is specific.

T Cell Receptors (TCRs) are heterodimeric, antigen-binding molecules typically comprising an α-chain and a β-chain. In nature, α-chains and β-chains are expressed at the cell surface of T cells (αβ T cells) as a complex with invariant CD3 chains. An alternative TCR comprising γ and δ chains is expressed on a subset of T cells (γδ T cells). TCRs recognise (bind to) antigen peptide presented by major histocompatibility complex (MHC) molecules. TCR structure and recognition of the peptide-MHC complex is described in detail for example in Immunobiology, 5$^{th}$ Edn. Janeway C A Jr, Travers P, Walport M, et al. New York: Garland Science (2001), Chapters 3 and 6, which are hereby incorporated by reference in their entirety.

T cells may be characterised by reference to surface expression of one or more of: a TCR polypeptide (e.g. α, β, γ or δ chain), a CD3 polypeptide (e.g. γ, δ or ε chain), CD8, and CD4. Surface expression of a given polypeptide can be measured by various methods well known in the art, e.g. by antibody-based methods such as immunohistochemistry, immunocytochemistry, and flow cytometry.

T cells expanded according to the methods of the present invention comprise a TCR specific for a virus. In some embodiments the T cells are CD3+ CD8+ T cells. In some embodiments, the T cells are cytotoxic T cells. In some embodiments, the T cells are CD3+ CD4+ T cells. In some embodiments, the T cells are helper T cells. In some embodiments, the methods of the present invention are for generating and/or expanding a population of virus-specific cytotoxic T lymphocytes (CTLs) and helper T lymphocytes.

CTLs are capable of effecting cell death in cells infected with a virus by releasing cytotoxic factors including perforin, granzymes, granulysin, and/or by inducing apoptosis of the infected cell by ligating FAS on the infected cell through FASL expressed on the T cell (described for example by Chavez-Galan et al., Cellular and Molecular Immunology (2009) 6(1): 15-25, hereby incorporated by reference in its entirety). Cytotoxicity can be investigated, for example, using any of the methods reviewed in Zaritskaya et al., Expert Rev Vaccines (2011), 9(6):601-616, hereby incorporated by reference in its entirety. One example of an assay for cytotoxicity of a T cell for to a target cell is the $^{51}$Cr release assay, in which target cells are treated with $^{51}$Cr, which they internalise. Lysis of the target cells by T cells results in the release of the radioactive $^{51}$Cr into the cell culture supernatant, which can be detected.

The peptide of the virus presented by the APCs may be derived from a viral particle, or may be encoded by nucleic acid of the virus. As used herein a "peptide" refers to a chain of two or more amino acid monomers linked by peptide bonds, which is 50 amino acids or fewer in length.

The viral peptide is presented by an MHC class I or class II molecule. MHC class I molecules are heterodimers of an α-chain and a β2-microglobulin. The α-chain has three domains designated α1, α2 and α3. The α1 and α2 domains together form the groove to which the peptide presented by the MHC class I molecule binds, to form the peptide-MHC complex. MHC class I α-chains are polymorphic, and different α-chains are capable of binding and presenting different peptides. Similar to MHC class I molecules, MHC class II molecules are also heterodimers, and consist of an α-chain and a β chain. In humans, MHC class I α-chains, and MHC class II α and β-chains are encoded by human leukocyte antigen (HLA) genes.

The virus-specific T cells according to the present disclosure comprise a TCR which is capable of binding to a peptide of the virus for which the T cell is specific, presented by an MHC class I or MHC class II molecule.

The virus for which the T cells are specific may be a dsDNA virus (e.g. adenovirus, herpesvirus, poxvirus), ssRNA virus (e.g. parvovirus), dsRNA virus (e.g. reovirus), (+)ssRNA virus (e.g. picornavirus, togavirus), (−)ssRNA virus (e.g. orthomyxovirus, rhabdovirus), ssRNA-RT virus (e.g. retrovirus) or dsDNA-RT virus (e.g. hepadnavirus). The present disclosure contemplates viruses of the families adenoviridae, herpesviridae, papillomaviridae, polyomaviridae, poxviridae, hepadnaviridae, parvoviridae, astroviridae, caliciviridae, picornaviridae, coronaviridae, flaviviridae, togaviridae, hepeviridae, retroviridae, orthomyxoviridae, arenaviridae, bunyaviridae, filoviridae, paramyxoviridae, rhabdoviridae and reoviridae.

Viruses associated with a disease or disorder are of particular interest. Accordingly, the following viruses are contemplated: adenovirus, Herpes simplex type 1 virus, Herpes simplex type 2 virus, Varicella-zoster virus, Epstein-Barr virus, Human cytomegalovirus, Human herpesvirus type 8, Human papillomavirus, BK virus, JC virus, Smallpox, Hepatitis B virus, Parvovirus B19, Human Astrovirus, Norwalk virus, coxsackievirus, hepatitis A virus, poliovirus, rhinovirus, severe acute respiratory syndrome virus, hepatitis C virus, yellow fever virus, dengue virus, West Nile virus, TBE virus, Rubella virus, Hepatitis E virus, Human immunodeficiency virus, influenza virus, lassa virus, Crimean-Congo hemorrhagic fever virus, Hantaan virus, ebola virus, Marburg virus, measles virus, mumps virus, parainfluenza virus, respiratory syncytial virus, rabies virus, hepatitis D virus, rotavirus, orbivirus, coltivirus, and banna virus.

In some embodiments, the virus is Epstein-Barr virus (EBV). Accordingly, in some embodiments the method is for generating or expanding a population of EBV-specific T cells.

In some embodiments, the EBV is strain B95-8, P3HR-1, or a derivative thereof.

In the present invention, the viral peptide is presented by an antigen presenting cell (APC). APCs process polypeptides by the molecular machinery to peptides which then become associated with MHC molecules and presented as peptide-MHC complexes at the cell surface. Different TCRs display different ability to bind to, and therefore different reactivity to, different peptide-MHC complexes.

Viral peptides/polypeptides are processed and presented in complex with MHC molecules. Antigen processing, loading and presentation on MHC is described in detail in, for example, Immunobiology, 5$^{th}$ Edn. Janeway C A Jr, Travers P, Walport M, et al. New York: Garland Science (2001), Chapter 5, hereby incorporated by reference in entirety.

Different kinds of T cells are activated through their TCRs by recognition of MHC-peptide complexes. CD8+ T cells recognize peptide-MHC class I complexes, whilst CD4+ T cells recognize peptide-MHC class II complexes. T cell activation requires binding MHC-peptide complex for which the TCR of the T cell has high affinity in the context of a positive costimulatory signal from APC. The process of T cell activation is well known to the skilled person and described in detail, for example, in Immunobiology, 5$^{th}$ Edn. Janeway C A Jr, Travers P, Walport M, et al. New York: Garland Science (2001), Chapter 8, which is incorporated by reference in its entirety.

APCs according to the invention may be professional APCs. Professional APCs are specialised for presenting antigen to T cells; they are efficient at processing and presenting MHC-peptide complexes at the cell surface, and express high levels of costimulatory molecules. Professional APCs include dendritic cells (DCs), macrophages, and B cells. Non-professional APCs are other cells capable of presenting MHC-peptide complexes to T cells, in particular MHC Class I-peptide complexes to CD8+ T cells.

In connection with the present invention, the APC may be any cell which is infected with, or comprising or expressing a peptide of, the virus for which the T cell comprises a specific TCR. The cell infected with, or comprising or expressing a peptide of, the virus may present a peptide of the virus in the context of an MHC molecule at the cell surface.

It will be appreciated that reference to "a peptide" herein encompasses plural peptides. For example, APCs presenting a peptide of the virus may present plural peptides of the virus.

The APCs may comprise an HLA allele encoding a MHC class I or class II molecule capable of presenting the peptide of the virus for which a TCR of the T cell is specific. In some embodiments the APCs may be HLA matched for the viral peptide recognised by a TCR of the T cell.

In some embodiments the APCs may express or comprise a peptide of the virus as a result of being infected with the virus. In some embodiments the APCs may have been modified to comprise or express a peptide of the virus. For example, in some embodiments the cell may have been modified to comprise nucleic acid encoding a peptide of the virus, or may have been pulsed with a peptide of the virus.

In some embodiments, viral peptide(s) may be provided to the APCs in a library of peptide mixtures, which may be referred to as pepmixes. In some embodiments, there is pooling of a variety of pepmixes for exposure to APCs. APCs presenting a peptide of the virus may be exposed to peripheral blood T-cells under certain conditions to result in stimulation of T-cells specific for the certain viral peptide(s).

In some embodiments, the APCs are B cells or are derived from B cells. In particular embodiments, the APCs may be cells of a lymphoblastoid cell line (LCL).

LCLs can be prepared by viral transformation of B cells. LCLs are typically produced by transformation of B cells with Epstein-Barr virus. Generation and characteristics of LCLs is described in detail, for example, in Hui-Yuen et al., J Vis Exp (2011) 57: 3321, and Hussain and Mulherkar, Int J Mol Cell Med (2012) 1(2): 75-87, both hereby incorporated by reference in entirety. Briefly, LCLs can be produced by incubation of PBMCs with concentrated cell culture supernatant of cells producing EBV, for example B95-8 cells, in the presence of cyclosporin A.

In some embodiments the APCs are obtained from, or are derived from cells obtained from, the same subject as the subject from which the population of T cells is generated or expanded. That is, in some embodiments the APCs and T cells are of autologous origin. In some embodiments, the APCs are obtained from, or are derived from cells obtained from, a different subject to the subject from which the population of T cells is generated or expanded. That is, in some embodiments the APCs and T cells are of heterologous origin.

In some embodiments according to the present invention, the APCs are LCLs prepared by transformation of B cells with EBV, wherein the B cells are obtained from the same subject as the T cells used in the methods of the invention. In some embodiments the LCLs are prepared by transformation of B cells obtained from a different subject to the subject from which the T cells are obtained.

In some embodiments, the B cells used for the preparation of LCLs may be obtained from a population of peripheral blood mononuclear cells (PBMCs) which is obtained from the same individual as the population of PBMCs from which the population of virus-specific T cells according to the invention is generated and/or expanded. In some embodiments, the B cells used for the preparation of LCLs is obtained from the same population of PBMCs from which the population of virus-specific T cells according to the invention is generated and/or expanded.

In some embodiments, the APCs (e.g. the LCLs) are irradiated or treated with a substance (e.g. mitomycin C) to prevent their proliferation, prior to culture in the presence of the T cells. Irradiation of LCLs in accordance with the present methods is typically at 6000 to 12000 rads.

The present methods are useful for producing large numbers of virus-specific T cells in a shorter period time relative to prior art methods for generation/expansion of virus-specific T cells. In particular, the methods are useful for producing large numbers of virus-specific T cells for adoptive transfer of the virus-specific T cells for treatment or prophylaxis of diseases caused or exacerbated by the virus, or for which infection with the virus is a risk factor.

For example, when the methods are for generating and/or expanding a population of EBV-specific T cells, the cells are useful to treat an EBV associated disorder such as nasopharangeal carcinoma (NPC) by adoptive transfer, e.g. as described in Chia W K et al., Molecular Therapy (2014), 22(1): 132-139, herein incorporated by reference in its entirety.

Adoptive transfer of T cells generally refers to a process by which T cells are obtained from a subject, typically by drawing a blood sample. The T cells are then typically treated or altered in some way, and either returned to the same subject or introduced into a different subject.

The treatment is typically aimed at providing a T cell population with certain desired characteristics to a subject, or increasing the frequency of T cells with such characteristics in that subject. Adoptive transfer of virus specific T cells is described, for example, in Cobbold et al., (2005) J. Exp. Med. 202: 379-386 and Rooney et al., (1998), Blood 92:1549-1555, hereby incorporated by reference in its entirety.

A subject herein may be a human. In some embodiments, a subject may be a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate).

Stimulating T Cells

In the present invention, populations of T cells are generated and/or expanded. The methods generally comprise steps of stimulating T cells, resulting in their cell division and therefore an increase their number.

A population of T cells may be generated from a single T cell by stimulation and consequent cell division. An existing population of T cells may be expanded by stimulation and consequent cell division of cells of the population of T cells.

APCs presenting a peptide of the virus preferentially stimulate T cells specific for the virus (i.e. T cells having a TCR capable of recognising viral peptide presented by the APC), and stimulation therefore causes cell division and proliferation of these cells over e.g. other T cells which do not comprise/express a TCR specific for the virus. The population of cells at the end of a stimulation is therefore enriched for T cells specific for the virus as compared to the population of cells prior to stimulation; that is, the virus-specific T cells are present at an increased frequency in the population of cells following stimulation. In this way, a population of T cells specific for the virus is expanded/generated out of a heterogeneous population of T cells having different specificities.

T cells are stimulated to proliferate by cell division following activation. As described hereinabove, T cell activation occurs through binding MHC-peptide complex for which the TCR of the T cell has high affinity in the context of a positive costimulatory signal from APC.

Activation induces T cells to produce IL-2, which promotes cell division. T cell activation also upregulates expression of the receptor for IL-2, and so proliferation of activated T cells is promoted in an autocrine fashion.

The methods of the present invention involve steps of stimulating and re-stimulating T cells using APCs presenting a peptide of the virus for which the T cell is specific. The stimulating APCs are infected with, or comprise or express a peptide of, the virus for which the T cell comprises a specific TCR, and present viral peptide in the context of an MHC molecule. Stimulation promotes cell division (i.e. causes the T cell(s) to proliferate), resulting in generation and/or expansion of a population of T cells specific for the virus.

A method step comprising "stimulating" and/or "re-stimulating" T cells by culture in the presence of APCs presenting a peptide of the virus may be referred to herein as a "stimulation step". The culture of T cells and APCs presenting a peptide of the virus in the context of a stimulation step according to the invention may be referred to herein as a "stimulation culture". As will be clear from the present disclosure, a stimulation culture of a stimulation step comprises cells in culture in media comprising cell culture media, and in many cases also comprising conditioned media.

Stimulating T cells according to the methods of the present invention involves culture of T cells in the presence of the APCs; i.e. co-culture of the T cells and APCs. Co-culture is typically performed in vitro or ex vivo.

In the present methods, a population of virus-specific T cells is typically generated from, or expanded out of, a population of PBMCs. Accordingly, in some embodiments of the methods of the present invention the T cells stimulated by culture in the presence of APCs are present in the culture with other PBMCs such as B cells, NK cells, and/or monocytes. In some embodiments, the population of T cells may be generated from, or expanded out of, a population of leukocytes, and may therefore be in culture with leukocytes other than T cells, such as B cells, NK cells, monocytes, neutrophils, eosinophils, and/or basophils.

The population of cells from which the population of virus-specific T cells is generated from, or expanded out of, may be referred to herein as "responders", and the APCs presenting a peptide of the virus may be referred to herein as "stimulators". In some embodiments, the stimulation steps of the present methods provide "responders" and "stimulators" at particular ratios, referred to herein as the "responder to stimulator ratio". As will be clear from the above, in some embodiments "responders" as used herein refers to a population of PBMCs. In some embodiments "responders" refers to a population of T cells, or leukocytes.

In the initial stimulation step, the "responders" are the population of cells comprising the T cells from which the population of virus-specific T cells is to be generated and/or expanded. The "responders" of an initial stimulation may e.g. be a population of T cells, a population of lymphocytes, a population of leukocytes, or a population of PBMCs. In particular embodiments, the "responders" of an initial stimulation are a population of PBMCs.

In stimulation steps subsequent to the initial stimulation step (i.e. steps of re-stimulating the T cells), the "responders" are the cells at the end of the preceding stimulation step, for example the cells collected at the end of the preceding stimulation step. The "responders" of a subsequent stimulation step will include viable cells in culture at the end of the preceding stimulation step, including the cells which have been stimulated to divide.

For example, in a method comprising the following steps:
(i) stimulating T cells by culture in the presence of APCs presenting a peptide of the virus;
(ii) collecting the cells obtained by step (i), and;
(iii) re-stimulating the T cells by culture in the presence of APCs presenting a peptide of the virus, wherein at least 10% of the media in which the cells are cultured is conditioned media obtained from a stimulation culture of T cells and APCs presenting a peptide of the virus;
the "responders" for stimulation of step (iii) are the cells collected at step (ii).

It will be appreciated that the "responder to stimulator ratio" refers to the relative number of cells at the beginning of a given stimulation step, i.e. the ratio of cells provided to the culture at the start of the stimulation step.

In some embodiments the "responders" of a re-stimulation step may include cells other than T cells; e.g. other PBMCs or leukocytes as described above. For example, in embodiments wherein the responders of an initial stimulation step of a method according to the invention are PBMCs, the cells collected at the end of said initial stimulation step may include PBMCs or leukocytes other than T cells.

Methods for expanding virus-specific T cells comprising multiple stimulation steps are well known to the skilled person. Typical culture conditions (i.e. cell culture media, additives, temperature, gaseous atmosphere), ratios of responders to stimulators, culture periods for stimulation steps, etc. can be readily determined by reference e.g. to Bollard et al., J Exp Med (2004), 200(12): 1623-1633 and Straathof et al., Blood (2005), 105(5): 1898-1904, both hereby incorporated by reference in entirety.

Co-culture of T cells and APCs in stimulation steps according to the invention is performed in cell culture media. The cell culture media can be any media in which T cells and APCs according to the invention can be maintained in culture in vitro/ex vivo. Culture media suitable for use in the culture of lymphocytes is well known to the skilled person, and includes, for example, AIM-V medium, Iscoves medium and RPMI-1640 medium.

As used herein, "cell culture media" is distinct from "conditioned media". As will be clear from the fullness of the present disclosure, a culture comprising T cells and APCs according to the present invention may be established using substantially only cell culture media (e.g. in an initial stimulation step), or may comprise both cell culture media and conditioned media (e.g. in a subsequent stimulation step).

In some embodiments, cell culture media may comprise RPMI-1640 medium and/or Click's medium (also known as Eagle's Ham's amino acids (EHAA) medium). The compositions of these media are well known to the skilled person. The formulation of RPMI-1640 medium is described in e.g. Moore et al., JAMA (1967) 199:519-524, and the formulation of Click's media is described in Click et al., Cell Immunol (1972) 3:264-276. RPMI-1640 medium can be obtained from e.g. ThermoFisher Scientific, and Click's medium can be obtained from e.g. Sigma-Aldrich (Catalog No. C5572).

In some embodiments, the cell culture media comprises RPMI-1640 medium and Click's medium. In some embodiments the cell culture media comprises (by volume) 25-65% RPMI-1640 medium, and 25-65% Click's medium. In some embodiments the cell culture media comprises 30-60% RPMI-1640 medium, and 30-60% Click's medium. In some embodiments the cell culture media comprises 35-55% RPMI-1640 medium, and 35-55% Click's medium. In some embodiments the cell culture media comprises 40-50% RPMI-1640 medium, and 40-50% Click's medium. In some embodiments the cell culture media comprises 45% RPMI-1640 medium, and 45% Click's medium.

In some embodiments the cell culture media may comprise one or more cell culture media additives. Cell culture media additives are well known to the skilled person, and include antibiotics (e.g. penicillin, streptomycin), serum (e.g. fetal bovine serum (FBS), bovine serum albumin (BSA)), L-glutamine, cytokines/growth factors, etc.

In some embodiments, the cell culture media comprises (by volume) 5-20% FBS, 7.5-15% FBS, or 10% FBS. In some embodiments, the cell culture media comprises 1-5 mM L-glutamine, 1.5-3 mM L-glutamine or 2 mM glutamine.

In some embodiments, the cell culture media for a stimulation step may comprise IL-2. In some embodiments IL-2 may be added (referred to herein as "added IL-2"). In some embodiments the IL-2 may be exogenous, i.e. IL-2 which is not produced by cells of the culture. In some embodiments the IL-2 may be recombinant IL-2.

In some embodiments, the cell culture media of a stimulation step according to the present invention comprises added IL-2 at a final concentration of 10-200 IU/ml, 15-175 IU/ml, 20-150 IU/ml, 30-125 IU/ml, or 40-100 IU/ml. The final concentration is the concentration in the total volume of media in the culture of the stimulation step (including the cell culture media, and any conditioned media).

In some particular embodiments the cell culture media comprises 40-50% RPMI-1640 medium, 40-50% Click's medium, 5-20% FBS, 1-5 mM L-glutamine, and added IL-2 at a final concentration of 10-200 IU/ml. In some embodiments the cell culture media comprises 42.5-47.5% RPMI-1640 medium, 42.5-47.5% Click's medium, 7.5-15% FBS, 1.5-3 mM L-glutamine and added IL-2 at a final concentration of 20-150 IU/ml. In some embodiments the cell culture media comprises 45% RPMI-1640 medium, 45% Click's medium, 10% FBS, 2 mM L-glutamine and added IL-2 at a final concentration of 40-100 IU/ml.

A stimulation step according to the present invention typically involves co-culture of the T cells and APCs for a defined period of time. Suitably, the period of time is at least long enough for the APCs to stimulate the T cells to undergo cell division. In some embodiments the period of time is long enough for stimulation and at least a single cell division of a stimulated T cell.

In some embodiments, a stimulation step according to the methods of the present invention involves culture of the T cells and APCs for a period of one of at least 1 hour, at least 6 hours, at least 12 hours, at least 24 hours, at least 48 hours, at least 36 hours, at least 72 hours, at least 4 days, at least 5 days, at least 6 days, at least 8 days, at least 9 days, at least 10 days, at least 11 days, at least 12 days, at least 13 days, or at least 14 days. In some embodiments, a stimulation step involves culture of the T cells and APCs for a period of one of not more than 20 days, not more than 14 days, not more than 13 days, not more than 12 days, not more than 11 days, not more than 10 days, not more than 9 days, not more than 8 days, not more than 7 days, not more than 6 days, not more than 5 days, not more than 4 days, or not more than 72 hours.

In some embodiments, a stimulation step according to the methods of the present invention involves culture of the T cells and APCs for a period of one of 24 hours to 20 days, 48 hours to 14 days, and 3 to 12 days. In some embodiments, a stimulation step involves culture of the T cells and APCs for a period of one 7 to 14 days, 8 days to 13 days, and 9 to 12 days. In some embodiments, a stimulation step involves culture of the T cells and APCs for a period of one 1 to 8 days, 2 days to 6 days, and 3 to 4 days.

A stimulation step is typically ended by separating the cells in culture from the media in which they have been cultured. In some embodiments, the methods comprise a step of collecting the cells at the end of the stimulation step (i.e. collecting the cells obtained at the end of the preceding stimulation step). The end of a stimulation step is determined by the culture period for that step; for example, a method step comprising stimulating T cells by culture in the presence of APCs presenting a peptide of a virus for a period of 7 days is ended by collecting the cells at the end of the 7 day culture period.

In some embodiments of the methods according to the present invention a stimulation step is ended by diluting the culture, e.g. by the addition of cell culture media. In such embodiments, there need be no collection of cells, and a re-stimulation step according to the present invention may be established by adding cell culture media (and any other additives as described herein) in an amount appropriate to achieve the desired percentages/concentrations of cell culture media, conditioned media (and any additives) for the re-stimulation step.

At the end of the culture period of the stimulation step, the cells may be collected and separated from the cell culture supernatant. For cells grown in suspension culture (such as lymphocytes), the cells may be collected by centrifugation, and the cell culture supernatant may be separated from the cell pellet. The cell pellet may then be re-suspended in cell culture media, e.g. for a further stimulation step. In some embodiments, the cells may undergo a washing step after collection. A washing step may comprise re-suspending the cell pellet in isotonic buffer such as phosphate-buffered saline (PBS), collecting the cells by centrifugation, and discarding the supernatant.

Methods for generating and/or expanding a population of T cells specific for a virus according to the present invention typically involve more than a single stimulation step. There is no upper limit to the number of stimulation steps which may be performed in a method according to the present invention. In some embodiments the methods comprise more than 2, 3, 4 or 5 stimulation steps. In some embodiments, the methods comprise one of 2, 3, 4, 5, 6, 7, 8, 9, 10, 11, 12, 13, 14, or 15 stimulation steps.

The stimulation steps in a method according to the present invention may be different to one another.

The frequency of the virus-specific T cells to be expanded may be very low in the initial responder population (e.g. the sample of PBMCs obtained from a subject), and in subsequent steps the frequency of virus-specific T cells in the responder population is larger as a result of preceding stimulation(s). Accordingly, in some embodiments the methods provide a higher responder to stimulator ratio for an initial stimulation step than for subsequent (i.e. re-stimulation) steps.

In some embodiments, the ratio of responders to stimulators for an initial stimulation step is in the range of one of 10:1 to 80:1, 15:1 to 70:1, 20:1 to 65:1, 25:1 to 60:1, 30:1 to 50:1, 35:1 to 45:1, or 40:1. In some embodiments, the ratio of responders to stimulators for a re-stimulation step is in the range of one of 1:1 to 10:1, 1.5:1 to 8:1, 2:1 to 7:1, 2.5:1 to 6:1, 3:1 to 5:1, 3.5:1 to 4.5:1, or 4:1.

An initial stimulation step (i.e. the first stimulation step of the method) typically involves culture of the T cells and APCs for a period of time which is a longer period than the culture period for a subsequent stimulation step. The longer period of time allows for an appreciable increase in the number of virus-specific T cells from their generally low frequency in the responder population of the initial stimulation.

In some embodiments, an initial stimulation step involves culture of the T cells and APCs for a period of one of 7 to 14 days, 8 days to 13 days, and 9 to 12 days. In some embodiments, a subsequent stimulation step involves culture of the T cells and APCs for a period of one of 1 to 8 days, 2 days to 5 days, and 3 to 4 days.

In some embodiments, the culture of an initial stimulation step may not include added IL-2, whereas the culture of subsequent stimulation steps may include added IL-2.

In some embodiments, the methods comprise an initial stimulation step followed by 1, 2, 3, 4, 5, 6, 7, 8, 9, 10, 11, 12, 13, or 14 subsequent stimulation steps. In some embodiments, each of the subsequent stimulation steps involves culture of the T cells and APCs for the same or similar period of time. In some embodiments, each of the subsequent stimulation steps involves culture of the T cells and APCs at the same or similar ratio of responders to stimulators. In some embodiments, the culture of each of the subsequent stimulation steps comprises added IL-2 at the same or similar final concentration.

Conveniently, cultures of cells according to the present disclosure are maintained at 37° C. in a humidified atmosphere containing 5% $CO_2$. Cultures can be performed in any vessel suitable for the volume of the culture, e.g. in wells of a cell culture plate, cell culture flasks, a bioreactor, etc. The cells of cell cultures according to the present invention can be established and/or maintained at any suitable density, as can readily be determined by the skilled person. For example, cultures may be established at an initial density of ~0.5×10$^6$ to ~5×10$^6$ cells/ml of the culture (e.g. ~1×10$^6$ cells/ml).

Cells may be cultured in any suitable cell culture vessel. In some embodiments of the methods according to the various aspects of the present invention, cells are cultured in a bioreactor. In some embodiments, cells are cultured in a bioreactor described in Somerville and Dudley, Oncoimmunology (2012) 1(8):1435-1437, which is hereby incorporated by reference in its entirety. In some embodiments cells are cultured in a GRex cell culture vessel, e.g. a GRex flask or a GRex 100 bioreactor.

Conditioned Media

The present invention involves the culture of cells in conditioned media. "Conditioned media" refers to media which has been obtained by culture of cells in cell culture media. Conditioned media contains factors (e.g. cytokines, chemokines, growth factors etc.) secreted/released from the cultured cells. Conditioned media is produced by culturing cells in a culture medium for a time sufficient to condition the medium, and then collecting the conditioned medium.

Cultures of stimulation steps according to the invention may comprise a mixture of a cell culture media and conditioned media. That is, the media in which the cells of a stimulation culture (e.g. of a stimulation step) are established and cultured may comprise both cell culture media and conditioned media. The use of a mixture of a conditioned media and a fresh media may provide a more complex nutrient mixture which is beneficial to the cells in culture.

It will be appreciated that the composition of the conditioned media will depend on the cells, the period of time, the culture conditions, the use of any additives and the composition of the cell culture media used for culture from which the conditioned media is obtained.

In the present invention, the conditioned media is obtained from a stimulation culture comprising T cells and APCs.

In some embodiments the cell culture media and conditioned media of a stimulation culture according to the present methods may be the same except for the conditioned media having been conditioned.

In some embodiments according to the methods of the present invention, the conditioned media may be obtained from the culture of a stimulation step according to any embodiment described herein.

In some embodiments, the conditioned media is collected at the end point of a stimulation step. Conveniently, the conditioned media may be collected at the end point of a stimulation step at the time of collecting the cells. For example, conditioned media according to the invention may be obtained from the supernatant obtained by centrifugation to collect cells at the end of a stimulation step as described herein.

In some embodiments, the conditioned media included in the culture of a stimulation step (i.e. a stimulation culture) according to the invention is obtained from the culture of a stimulation step as described herein. In some embodiments, the conditioned media is not obtained from the culture of an initial stimulation step (i.e. the first stimulation step of a method according to the invention).

An appropriate culture period to condition a medium may be determined by the skilled person, based on known methods. Typically, a medium will be conditioned for between about 1 hour and about 8 days, such as between about 1 day to 8 days, 2 days to 5 days, or 3 to 4 days.

In particular embodiments, conditioned media according to the present invention is obtained from:
(1) A stimulation culture of virus-specific T cells in the presence of APCs presenting a peptide of the virus for which the T cells are specific;
(2) A stimulation culture according to (1), after a culture period of one of 1 to 8 days, 2 days to 6 days, and 3 to 4 days;
(3) A stimulation culture according to (1) or (2), at a responder:stimulator ratio of one of 1:1 to 10:1, 1.5:1 to 8:1, 2:1 to 7:1, 2.5:1 to 6:1, 3:1 to 5:1, 3.5:1 to 4.5:1, or 4:1;
(4) A stimulation culture according to any one of (1) to (3), wherein the cell culture medium used for the stimulation culture comprises 30-60% RPMI-1640 medium and/or 30-60% Click's medium and/or 5-20% FBS and/or 1-5 mM L-glutamine;
(5) A stimulation culture according to any one of (1) to (4), comprising added IL-2 at a final concentration of 10-200 IU/ml, 15-175 IU/ml, 20-150 IU/ml, 30-125 IU/ml, or 40-100 IU/ml;
(6) A stimulation culture according to any one of (1) to (5), additionally comprising at least 10% conditioned media obtained from a stimulation culture according to any one of (1) to (5);
(7) A stimulation culture according to any one of (1) to (6), wherein the APCs are LCLs, e.g. EBV-transformed LCLs.

In some embodiments, the conditioned media included in the culture of a given stimulation step may be obtained from the culture of another, different stimulation step of the same method. For example, conditioned media included in the culture of a third stimulation step of a method according to the invention may be obtained from the culture of the second stimulation step.

In some embodiments, the conditioned media included in the culture of a stimulation step may be obtained from the culture of the preceding stimulation step of the method. For example, conditioned media included in the culture of a third stimulation step may be obtained from the culture of the second stimulation step, and conditioned media included in the culture of a fourth stimulation step may be obtained from the culture of the third stimulation step, and so on.

In embodiments of the methods according to the present invention, not every stimulation step comprises culture in media including conditioned media. For example, in some embodiments the culture of the initial stimulation step according to the methods does not include conditioned media.

A culture of a stimulation step comprising conditioned media may contain conditioned media in an amount (by volume) of one of at least 2%, at least 5%, at least 7.5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the total volume of media in the culture of the stimulation step. The remaining volume may be made-up by cell culture media as described herein, including any additives thereto. In some embodiments, the conditioned media may comprise at least 10% of the total volume of media in the culture of the stimulation step.

Although conditioned media is rich in growth factors and cytokines it typically comprises a lower concentration of e.g. amino acids and glucose as compared to comparable cell culture media which has not been conditioned, due e.g. to consumption by the cells cultured in the medium. Conditioned media may also comprise waste products of the cells used to condition the media. Such factors may have a negative impact on cell growth and division, and so it may therefore be important that not 100% of the media in a stimulation culture of a stimulation step according to the invention is conditioned media. In some embodiments, a culture of a stimulation step comprising conditioned media may contain conditioned media in an amount (by volume) of one of less than 100%, less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, or less than 15% of the total volume of media in the culture of the stimulation step.

In some embodiments, the conditioned media may comprise up to 30%, up to 25%, up to 20% or up to 15% of the total volume of media in the culture of the stimulation step.

In some embodiments, the conditioned media may comprise one of 5 to 70%, 7.5 to 70%, 10 to 70%, 10 to 65% 10 to 60%, 12.5 to 55%, 15 to 50%, 15 to 45%, 15 to 40%, 17.5% to 45%, 20-40%, 20-35%, or 20-30% of the total volume of media in the culture of the stimulation step. In some embodiments, the conditioned media may comprise 20-30% of the total volume of media in the culture of the stimulation step. In some embodiments, the conditioned media may comprise 10 to 25%, preferably about 15% of the total volume of media in the culture of the stimulation step.

In some embodiments, the conditioned media may comprise one of 5 to 30%, 5 to 27.5%, 5 to 25%, 5 to 22.5%, 5 to 20%, or 5 to 17.5% of the total volume of media in the culture of the stimulation step. In some embodiments, the conditioned media may comprise one of 7.5 to 30%, 10 to 30% or 12.5 to 30% of the total volume of media in the culture of the stimulation step.

In some embodiments, the conditioned media may comprise one of 5 to 30%, 10 to 25%, 10 to 20%, 12.5 to 17.5% or about 15% of the total volume of media in the culture of the stimulation step.

In some embodiments, the conditioned media may comprise one of about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29% or 30% of the total volume of media in the culture of the stimulation step.

Culture media may be a 1× formulation or a concentrated formulation, e.g. a 2× to 250× concentrated medium formulation. In a 1× formulation each ingredient in the medium is at the concentration intended for cell culture. In a concentrated formulation one or more of the ingredients is present at a higher concentration than intended for cell culture. Concentrated culture media is well known in the art. Culture media can be concentrated using known methods e.g. salt precipitation or selective filtration. A concentrated medium may be diluted for use with water (preferably deionized and distilled) or any appropriate solution, e.g. an aqueous saline solution, an aqueous buffer or culture media.

It will be appreciated that the indicated percentages are made with reference to a 1× formulation of conditioned media. The skilled person understands that a culture comprising 10% of a 1× formulation of conditioned media is equivalent to a culture comprising 1% of a 10× concentrated formulation of conditioned media.

In some embodiments, conditioned media may be collected from the culture of a stimulation step and stored, e.g. at −80° C. The stored conditioned media can then be thawed and used in a method according to the invention. In some embodiments the conditioned media may be treated to remove cells or debris, e.g. by filtration.

Specific Exemplary Embodiments of the Methods

In accordance with the present invention, several specific exemplary embodiments of the methods are provided. The following specific embodiments are for purely illustrative purposes, to show how the various features described hereinabove may be combined, and are not intended to in any way limit the present invention.

A method for generating or expanding, or a method for accelerating the rate of expansion of, a population of EBV-specific T cells (e.g. CTLs), comprising stimulating T cells (e.g. within a population of PBMCs) by culture in the presence of EBV-transformed LCLs (e.g. irradiated, EBV-transformed LCLs), at a responder to stimulator ratio of 2:1 to 7:1 (e.g. 4:1) for a period of 1 to 8 (e.g. 3 to 4) days, in media comprising:

(a) cell culture media comprising 40-50% (e.g. 45%) RPMI-1640 medium, 40-50% (e.g. 45%) Click's medium, 5-20% (e.g. 10%) FBS, and 1-5 mM (e.g. 2 mM) L-glutamine, (b) at least 10% (e.g. 10% to 70%) conditioned media obtained by a method comprising: stimulating T cells (e.g. within a population of PBMCs) by culture in the presence of EBV-transformed LCLs (e.g. e.g. irradiated, EBV-transformed LCLs), at a responder to stimulator ratio of 2:1 to 7:1 (e.g. 4:1) in cell culture media comprising 40-50% (e.g. 45%) RPMI-1640 medium, 40-50% (e.g. 45%) Click's medium, 5-20% (e.g. 10%) FBS, and 1-5 mM (e.g. 2 mM) L-glutamine, and added IL-2 at a final concentration of 10-200 (e.g. 40-100) IU/ml, for a period of 1 to 8 (e.g. 3 to 4) days, and (c) added IL-2 at a final concentration of 10-200 (e.g. 40-100) IU/ml.

A method for generating or expanding a population of EBV-specific T cells (e.g. CTLs), comprising:

(i) stimulating T cells (e.g. within a population of PBMCs) by culture in the presence of EBV-transformed LCLs (e.g. irradiated, EBV-transformed LCLs) at a responder to stimulator ratio of 10:1 to 80:1 (e.g. 40:1) in cell culture media comprising 40-50% (e.g. 45%) RPMI-1640 medium, 40-50% (e.g. 45%) Click's medium, 5-20% (e.g. 10%) FBS, and 1-5 mM (e.g. 2 mM) L-glutamine for a period of 7 to 14 (e.g. 9 to 12) days;

(ii) collecting the cells obtained by step (i);

(iii) re-stimulating the T cells by culturing cells collected at step (ii) in the presence of EBV-transformed LCLs (e.g. irradiated, EBV-transformed LCLs) at a responder to stimulator ratio of 2:1 to 7:1 (e.g. 4:1) in cell culture media comprising 40-50% (e.g. 45%) RPMI-1640 medium, 40-50% (e.g. 45%) Click's medium, 5-20% (e.g. 10%) FBS, and 1-5 mM (e.g. 2 mM) L-glutamine, and added IL-2 at a final concentration of 10-200 (e.g. 40-100) IU/ml, for a period of 1 to 8 (e.g. 3 to 4) days;

(iv) collecting the cells obtained by step (iii), and;

(v) re-stimulating the T cells by culturing cells collected at step (iv) in the presence of EBV-transformed LCLs (e.g. irradiated, EBV-transformed LCLs) at a responder to stimulator ratio of 2:1 to 7:1 (e.g. 4:1) for a period of 1 to 8 (e.g. 3 to 4) days in media comprising: (a) cell culture media comprising 40-50% (e.g. 45%) RPMI-1640 medium, 40-50% (e.g. 45%) Click's medium, 5-20% (e.g. 10%) FBS, and 1-5 mM (e.g. 2 mM) L-glutamine, (b) at least 10% (e.g. 10% to 70%) conditioned media obtained at the end point of step (iii), and (c) added IL-2 at a final concentration of 10-200 (e.g. 40-100) IU/ml.

In some embodiments, the method additionally comprises:

(vi) collecting the cells obtained by step (v), and;

(vii) re-stimulating the T cells by culturing cells collected at step (vi) in the presence of EBV-transformed LCLs (e.g. irradiated, EBV-transformed LCLs) at a responder to stimulator ratio of 2:1 to 7:1 (e.g. 4:1) for a period of 1 to 8 (e.g. 3 to 4) days in media comprising: (a) cell culture media comprising 40-50% (e.g. 45%) RPMI-1640 medium, 40-50% (e.g. 45%) Click's medium, 5-20% (e.g. 10%) FBS, and 1-5 mM (e.g. 2 mM) L-glutamine, (b) at least 10% (e.g. 10% to 70%) conditioned media obtained at the end point of step (v), and (c) added IL-2 at a final concentration of 10-200 (e.g. 40-100) IU/ml.

In some embodiments, the method comprises additional steps of collecting cells, and re-stimulating the T cells by culturing the collected cells in the presence of EBV-transformed LCLs (e.g. irradiated, EBV-transformed LCLs) at a responder to stimulator ratio of 2:1 to 7:1 (e.g. 4:1) for a period of 1 to 8 (e.g. 3 to 4) days in media comprising: (a) cell culture media comprising 40-50% (e.g. 45%) RPMI-1640 medium, 40-50% (e.g. 45%) Click's medium, 5-20% (e.g. 10%) FBS, and 1-5 mM (e.g. 2 mM) L-glutamine, (b)

at least 10% (e.g. 10% to 70%) conditioned media obtained at the end point of the preceding stimulation step, and (c) added IL-2 at a final concentration of 10-200 (e.g. 40-100) IU/ml.

Rates of Expansion

The present methods achieve an improved rate of expansion for populations of virus-specific T cells as compared to prior art methods.

The rate of expansion for a T cell population can be analysed by methods well known to the skilled person. Methods include measuring the number of T cells at one or more time points. For example, the number of T cells can be determined after performing a method according to the invention and compared to the number of T cells at the beginning of the method; fold expansion in the number of T cells can then be calculated.

Rates of expansion can also be determined by analysing cell division by T cells over a period of time. Cell division for a given population of T cells can be analysed, for example, by in vitro analysis of incorporation of $^3$H-thymidine or by CFSE dilution assay, e.g. as described in Fulcher and Wong, Immunol Cell Biol (1999) 77(6): 559-564, hereby incorporated by reference in entirety.

The improvement in the rate of expansion achieved by the methods according to the present invention can be determined by performing a method according to the invention, and comparing the expansion for T cells in that method to a comparable, control method lacking a stimulation culture in the presence of conditioned media.

For example, the rate of expansion can be compared between two methods: (i) a method according to the invention, comprising stimulating T cells by culture in the presence of APCs presenting a peptide of the virus, wherein at least 10% of the media in which the cells are cultured is conditioned media obtained from a stimulation culture comprising T cells and APCs presenting a peptide of the virus; and (ii) a comparable control method, which is the same except that cell culture media is used in place of the conditioned media.

In some embodiments, the rate of expansion for a population of T cells in a method according to the present invention is one of at least 1.001 times, 1.002 times, 1.003 times, 1.004 times, 1.005 times, 1.006 times, 1.007 times, 1.008 times, 1.009 times, 1.01 times, 1.02 times, 1.03 times, 1.04 times, 1.05 times, 1.06 times, 1.07 times, 1.08 times, 1.09 times, 1.1 times, 1.2 times, 1.3 times, 1.4 times, 1.5 times, 1.6 times, 1.7 times, 1.8 times, 1.9 times, or 2 times the rate of expansion in a comparable control method in which cell culture media is used in place of the conditioned media.

The rate of expansion may be of the virus-specific T cell population, or the total T cell population.

Properties of the Expanded Cells

Advantageously, the virus-specific T cells generated/expanded according to the method of the present invention retain the same functional properties as virus-specific T cells generated/expanded according to prior art methods. That is, the accelerated rate of expansion does not negatively influence the functional properties of the expanded T cells.

For example, in embodiments wherein the methods generate/expand a population of virus-specific CTLs, the CTLs display similar cytotoxicity to cells infected with or comprising/expressing a peptide of the virus as virus-specific CTLs expanded according to methods lacking stimulation culture in the presence of conditioned media.

Cytotoxicity of expanded CTLs can be analysed e.g. by culturing the expanded T cell population with APCs presenting a peptide of the virus for which the T cell is specific at different effector (i.e. T cell) to target (i.e. APC) ratios, and measuring specific lysis of the APCs. For example, cytotoxicity of an EBV-specific CTL population can be analysed by measuring specific lysis of EBV-transformed LCL cells at different effector to target ratios.

Therapeutic Applications

The present methods find application in methods of medical treatment. Treatment may be provided to subjects having a disease or condition in need of treatment.

In particular, methods for treating or preventing a disease or disorder (e.g. a cancer) are provided comprising a method for generating or expanding a population of T cells specific for a virus, or a method for accelerating the rate of expansion of a virus-specific T cell population, as described herein.

Methods of treatment or preventing a disease or disorder according to the present invention may comprise adoptive transfer of T cells.

In one aspect, the present invention provides a method of treating or preventing a disease or disorder in a subject, comprising:

(1) isolating T cells from a subject;
(2) generating or expanding a population of T cells specific for a virus as described herein, and;
(3) administering the generated or expanded population of T cells to a subject.

In some embodiments, the subject from which the T cells are obtained at step (1) of the method is the same subject as the subject to which the population of T cells generated or expanded according to the methods described herein are administered at step (3) of the method (i.e. adoptive transfer is of autologous T cells). In some embodiments, the subject from which the T cells are obtained at step (1) of the method is a different subject to the subject to which the population of T cells generated or expanded according to the methods described herein are administered at step (3) of the method (i.e., adoptive transfer is of allogenic T cells).

It will be appreciated that the T cells isolated from the subject according to step (1) above may be within a population of PBMCs.

In some embodiments, the method may comprise one or more of the following steps: taking a blood sample from a subject; isolating PBMCs from the blood sample; isolating T cells from the blood sample; generating or expanding a population of T cells specific for a virus according to the methods described herein; modifying the T cells, e.g. to express a chimeric antigen receptor (CAR) or T cell receptor (TCR); collecting the generated/expanded population of virus-specific T cells; mixing the generated/expanded population of virus-specific T cells with an adjuvant, diluent, or carrier; administering the generated/expanded population of virus-specific T cells to a subject.

The methods may comprise modification or treatment of the T cells in some way. For example, the T cell may be modified in vitro or ex vivo to express or comprise a chimeric antigen receptor (CAR) or T cell receptor (TCR). T cells can be modified according to methods well known to the skilled person. The modification may comprise nucleic acid transfer for permanent or transient expression of the transferred nucleic acid. Any suitable genetic engineering platform may be used for such modification. Suitable methods include the use of genetic engineering platforms such as gammaretroviral vectors, lentiviral vectors, adenovirus vectors, DNA transfection, transposon-based gene delivery and RNA transfection, for example as described in Maus et al., Annu Rev Immunol (2014) 32:189-225, hereby incorporated by reference in its entirety.

The treatment may be aimed at prevention of a disease/disorder, and as such the virus-specific T cells generated/expanded according to the method of the present invention may be employed prophylactically against development of a disease state. This may take place before the onset of symptoms of the disease state, and/or may be given to subjects considered to be at greater risk of the disease or disorder.

The disease or condition may be one which is caused or exacerbated by infection with a virus for which the T cells generated/expanded according to the method of the present invention are specific. In some embodiments, the disease or condition may be one which is caused or exacerbated by infection with a virus described herein.

In particular, the disease or condition may be one which is caused or exacerbated by Epstein-Barr virus (EBV), influenza virus, measles virus, hepatitis B virus (HBV), hepatitis C virus (HCV), human immunodeficiency virus (HIV), lymphocytic choriomeningitis virus (LCMV), Herpes simplex virus (HSV) or human papilloma virus (HPV).

Virus-specific T cells generated/expanded according to the method of the present invention are useful in methods for the treatment or prevention of cancer. Accordingly, in some embodiments the method of treatment or prevention of a disease or disorder is for treating or preventing a cancer.

Methods of medical treatment may involve treatment of cancer by a method of ameliorating, treating, or preventing a malignancy in a human subject wherein the steps of the method assist or boost the immune system in eradicating cancerous cells. Such methods may include the administration of virus-specific T cells generated/expanded according to the method of the present invention that invoke an active (or achieve a passive) immune response to destroy cancerous cells. Methods of treatment may optionally include the co-administration of biological adjuvants (e.g., interleukins, cytokines, Bacillus Comette-Guerin, monophosphoryl lipid A, etc.) in combination with conventional therapies for treating cancer such as chemotherapy, radiation, or surgery. Methods of treatment may involve administering virus-specific T cells generated/expanded according to the method of the present invention as a vaccine that works by activating the immune system to prevent or destroy cancer cell growth. Methods of medical treatment may involve in vivo, ex vivo, and adoptive immunotherapies, including those using autologous and/or heterologous cells or immortalized cell lines.

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, haematologic cancer and sarcoma.

In particular, treatment of head and neck cancer, nasopharyngeal carcinoma (NPC), oropharyngeal cancer (OPC), cervical cancer (CC), gastric/stomach cancer or lung cancer is contemplated.

In some embodiments the cancer is an EBV- or HPV-positive cancer. In some embodiments, the cancer is EBV-positive NPC. In some embodiments, the cancer is HPV-positive OPC or HPV-positive CC.

Administration of virus-specific T cells generated/expanded according to the method of the present invention is preferably in a "therapeutically effective amount", this being sufficient to show benefit to the individual. The actual amount administered, and rate and time-course of administration, will depend on the nature and severity of the disease being treated.

Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Formulating Pharmaceutically Useful Compositions and Medicaments

Virus-specific T cells generated/expanded according to the method of the present invention may be formulated for clinical use and may comprise a pharmaceutically acceptable carrier, diluent, excipient or adjuvant.

In accordance with the present invention methods are also provided for the production of pharmaceutically useful compositions comprising virus-specific T cells generated/expanded according to the method of the present invention, such methods of production may comprise one or more steps selected from: generating/expanding a population of virus-specific T cells according to the methods of the present invention; and/or mixing virus-specific T cells generated/expanded according to the methods of the present invention with a pharmaceutically acceptable carrier, adjuvant, excipient or diluent.

Subjects

The subject to be treated may be any animal or human. The subject is preferably mammalian, more preferably human. The subject may be a non-human mammal, but is more preferably human. The subject may be male or female. The subject may be a patient.

A subject may have been diagnosed with a disease or condition requiring treatment, may be suspected of having such a disease or condition, or may be at risk of developing such a disease or condition.

Statements of Broad Inventive Technical Features of the Present Invention

The following numbered paragraphs provide contain statements of broad combinations of the inventive technical features herein disclosed:

1. A method for generating or expanding a population of T cells specific for a virus, comprising stimulating T cells by culture in the presence of antigen presenting cells (APCs) presenting a peptide of the virus, wherein at least 10% of the media in which the cells are cultured is conditioned media obtained from a stimulation culture comprising T cells and APCs presenting a peptide of the virus.

2. A method for accelerating the rate of expansion of a virus-specific T cell population, the method comprising stimulating T cells by culture in the presence of antigen presenting cells (APCs) presenting a peptide of the virus, wherein at least 10% of the media in which the cells are cultured is conditioned media obtained from a stimulation culture comprising T cells and APCs presenting a peptide of the virus.

3. A method for generating or expanding a population of T cells specific for a virus, comprising:
   (i) stimulating T cells by culture in the presence of antigen presenting cells (APCs) presenting a peptide of the virus; and
   (ii) re-stimulating the T cells by culture in the presence of APCs presenting a peptide of the virus, wherein at least 10% of the media in which the cells are cultured is conditioned media obtained from a stimulation culture of T cells and APCs presenting a peptide of the virus.

4. A method for generating or expanding a population of T cells specific for a virus, comprising:
   (i) stimulating T cells by culture in the presence of antigen presenting cells (APCs) presenting a peptide of the virus;
   (ii) collecting the cells obtained by step (i), and;
   (iii) re-stimulating the T cells by culture in the presence of APCs presenting a peptide of the virus, wherein at least 10% of the media in which the cells are cultured is conditioned media obtained from a stimulation culture of T cells and APCs presenting a peptide of the virus.

5. A method for generating or expanding a population of T cells specific for a virus, wherein the method comprises:
   (i) stimulating T cells by culture in the presence of antigen presenting cells (APCs) presenting a peptide of the virus;
   (ii) collecting the cells obtained by step (i);
   (iii) re-stimulating the T cells by culture in the presence of APCs presenting a peptide of the virus;
   (iv) collecting the cells obtained by step (iii); and
   (v) re-stimulating the T cells by culture in the presence of APCs presenting a peptide of the virus, wherein at least 10% of the media in which the cells are cultured is conditioned media obtained from a stimulation culture of T cells and APCs presenting a peptide of the virus.

6. The method according to paragraph 5, wherein the conditioned media is obtained from the stimulation culture of step (iii).

7. The method according to any one of paragraphs 1 to 6, wherein the conditioned media is obtained from a stimulation culture of T cells and APCs presenting a peptide of the virus after a culture period of 1 to 8 days.

8. The method according to any one of paragraphs 1 to 7, wherein the conditioned media is obtained from a stimulation culture of T cells and APCs at a responder:stimulator ratio of 1:1 to 10:1.

9. The method according to any one of paragraphs 1 to 8, wherein the APCs presenting a peptide of the virus are EBV-transformed lymphoblastoid cell line (LCL) cells.

10. The method according to any one of paragraphs 1 to 9, wherein the at least 10% of conditioned media is 20 to 40% of conditioned media.

11. A method for generating or expanding a population of Epstein-Barr Virus (EBV)-specific T cells, comprising stimulating T cells by culture in the presence of EBV-transformed LCLs at a responder to stimulator ratio of 2:1 to 7:1 for a period of 1 to 8 days, in media comprising:
   (a) cell culture media comprising 40-50% RPMI-1640 medium, 40-50% Click's medium, 5-20% FBS, and 1-5 mM L-glutamine,
   (b) at least 10% conditioned media obtained by a method comprising: stimulating T cells by culture in the presence of EBV-transformed LCLs at a responder to stimulator ratio of 2:1 to 7:1 in cell culture media comprising 40-50% RPMI-1640 medium, 40-50% Click's medium, 5-20% FBS, and 1-5 mM L-glutamine, and added IL-2 at a final concentration of 10-200 IU/ml, for a period of 1 to 8 days, and
   (c) added IL-2 at a final concentration of 10-200 IU/ml.

12. A method for accelerating the rate of expansion of a population of Epstein-Barr Virus (EBV)-specific T cells, comprising stimulating T cells by culture in the presence of EBV-transformed LCLs at a responder to stimulator ratio of 2:1 to 7:1 for a period of 1 to 8 days, in media comprising:
   (a) cell culture media comprising 40-50% RPMI-1640 medium, 40-50% Click's medium, 5-20% FBS, and 1-5 mM L-glutamine,
   (b) at least 10% conditioned media obtained by a method comprising: stimulating T cells by culture in the presence of EBV-transformed LCLs at a responder to stimulator ratio of 2:1 to 7:1 in cell culture media comprising 40-50% RPMI-1640 medium, 40-50% Click's medium, 5-20% FBS, and 1-5 mM L-glutamine, and added IL-2 at a final concentration of 10-200 IU/ml, for a period of 1 to 8 days, and
   (c) added IL-2 at a final concentration of 10-200 IU/ml.

13. A method for generating or expanding a population of Epstein-Barr Virus (EBV)-specific T cells, comprising:
   (i) stimulating T cells by culturing PBMCs in the presence of EBV-transformed LCLs at a responder to stimulator ratio of 10:1 to 80:1 in cell culture media comprising 40-50% RPMI-1640 medium, 40-50% Click's medium, 5-20% FBS, and 1-5 mM L-glutamine for a period of 7 to 14 days;
   (ii) collecting the cells obtained by step (i);
   (iii) re-stimulating the T cells by culturing cells collected at step (ii) in the presence of EBV-transformed LCLs at a responder to stimulator ratio of 2:1 to 7:1 in cell culture media comprising 40-50% RPMI-1640 medium, 40-50% Click's medium, 5-20% FBS, and 1-5 mM L-glutamine, and added IL-2 at a final concentration of 10-200 IU/ml, for a period of 1 to 8 days;
   (iv) collecting the cells obtained by step (iii), and;
   (v) re-stimulating the T cells by culturing cells collected at step (iv) in the presence of EBV-transformed at a responder to stimulator ratio of 2:1 to 7:1 for a period of 1 to 8 days in media comprising: (a) cell culture media comprising 40-50% RPMI-1640 medium, 40-50% Click's medium, 5-20% FBS, and 1-5 mM L-glutamine, (b) at least 10% conditioned media obtained at the end point of step (iii), and (c) added IL-2 at a final concentration of 10-200 (e.g. 40-100) IU/ml.

14. The method according to paragraph 13, wherein the method additionally comprises:
(vi) collecting the cells obtained by step (v), and;
(vii) re-stimulating the T cells by culturing cells collected at step (vi) in the presence of EBV-transformed LCLs at a responder to stimulator ratio of 2:1 to 7:1 for a period of 1 to 8 days in media comprising: (a) cell culture media comprising 40-50% RPMI-1640 medium, 40-50% Click's medium, 5-20% FBS, and 1-5 mM L-glutamine, (b) at least 10% conditioned media obtained at the end point of step (v), and (c) added IL-2 at a final concentration of 10-200 (e.g. 40-100) IU/ml.

15. The method according to paragraph 13 or 14, wherein the method comprises additional steps of collecting cells, and re-stimulating the T cells by culturing the collected cells in the presence of EBV-transformed LCLs (e.g. irradiated, EBV-transformed LCLs) at a responder to stimulator ratio of 2:1 to 7:1 for a period of 1 to 8 days in media comprising: (a) cell culture media comprising 40-50% RPMI-1640 medium, 40-50% Click's medium, 5-20% FBS, and 1-5 mM L-glutamine, (b) at least 10% conditioned media obtained at the end point of the preceding stimulation step, and (c) added IL-2 at a final concentration of 10-200 IU/ml.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures in which.

EXAMPLES

In the following Examples the inventors describe expansion of EBV-specific T cells including culture in the presence of conditioned media. The inventors describe experiments for determining the optimum percentage of conditioned media to include in cultures, and for confirming cytotoxic activity of the expanded CTLs.

Example 1: Optimum Percentage of Conditioned Media

To determine the optimum percentage of conditioned medium for T cell expansion, in T cell expansions performed in 24 well plates, cell culture media comprising 45% RPMI 1640, 45% Click's media, 10% FBS, 2 mM L-glutamine is mixed with 10%, 20%, 30%, 40%, 50%, and 60% of conditioned medium obtained from a co-culture of T cells with LCL cells.

After one week of co-culture with LCL cells, the number of T cells is counted and compared to the number of seeded cells, to determine fold expansion.

Figure 1A:
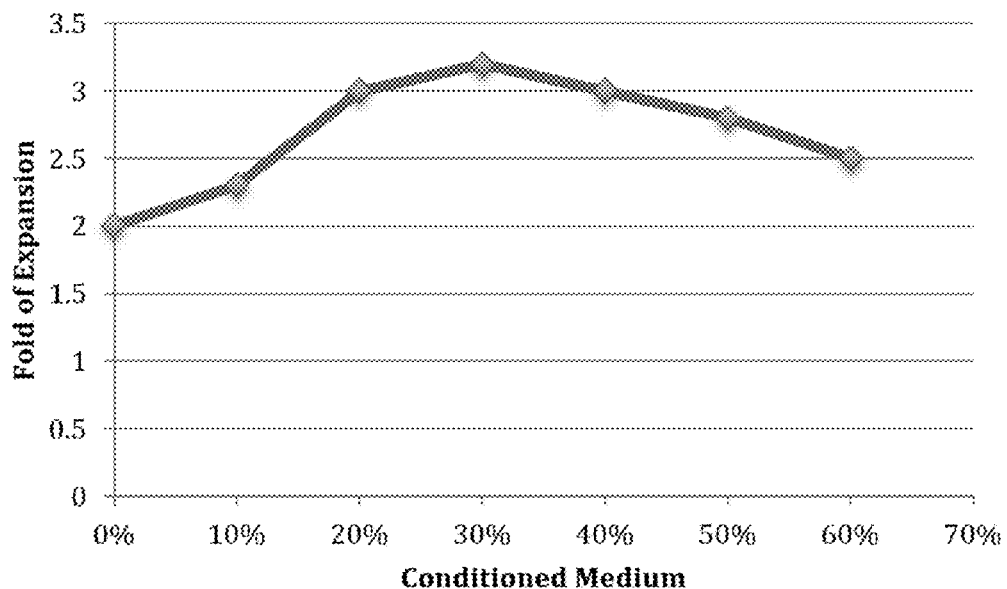
FIGS. 1A and FIG. 1B. Graph showing the effect of conditioned media on EBV-specific T cell expansion from cells obtained from (1A) Donor 1 and (1B) Donors 2 and 3. Increasing percentages of conditioned media are added to culture media. After one week of co-culture with LCL, the number of expanded T cells is compared to the original number of seeded T cells.

The expected expansion results are shown on FIG. 1A. T cells are expanded at a faster rate by the methods including culture in the presence of conditioned media. The optimum percentage of conditioned media in a method step according to B for greatest fold expansion is expected to be 20-30% conditioned media.

Figure 1B:
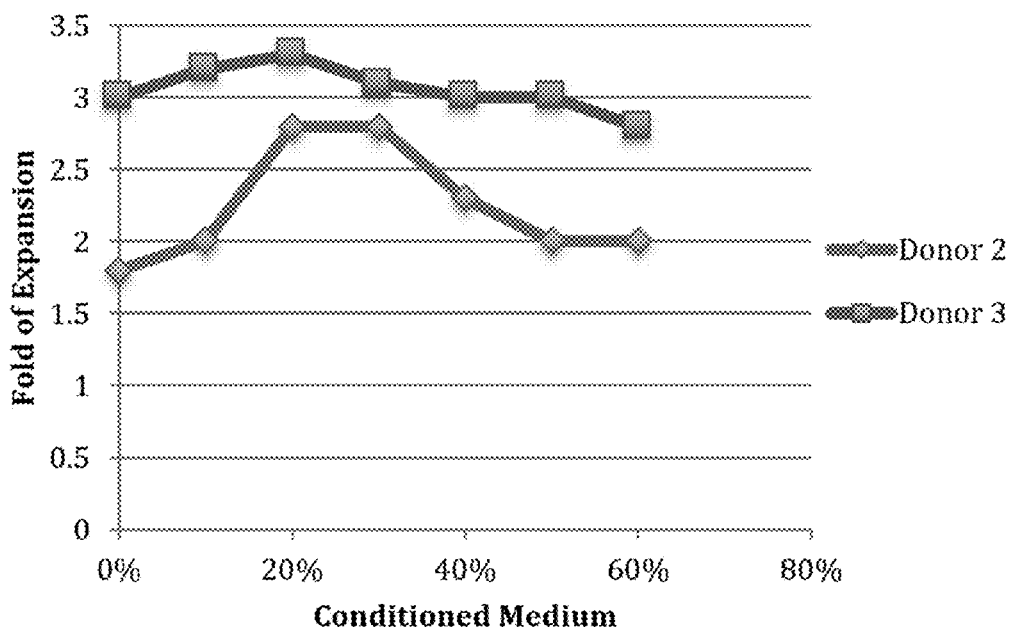

The same experiment is performed on cells obtained from two further, different donors (Donors 2 and 3). It is expected that the results will be similar as for the Donor 1, with maximum T cell expansion observed at 20-30% conditioned media (see FIG. 1B).

Because large-scale expansion of T cells will be performed in bioreactors such as e.g. Grex-100 culture vessels, the optimised percentage of conditioned media is further investigated in bioreactor culture.

For Illustrative Purposes:

Cells are cultured at a cell density of $1 \times 10^6$ cells/ml in 200 ml of media, of which varying percentages are conditioned media:

| Cell culture media comprising 45% RPMI 1640, 45% Click's media, 10% FBS, 2 mM L-glutamine | Conditioned media | % Conditioned media |
|---|---|---|
| 160 ml | 40 ml | 20% |
| 140 ml | 60 ml | 30% |
| 120 ml | 80 ml | 40% |
| 100 ml | 100 ml | 50% |
| 80 ml | 120 ml | 60% |

Figure 2:
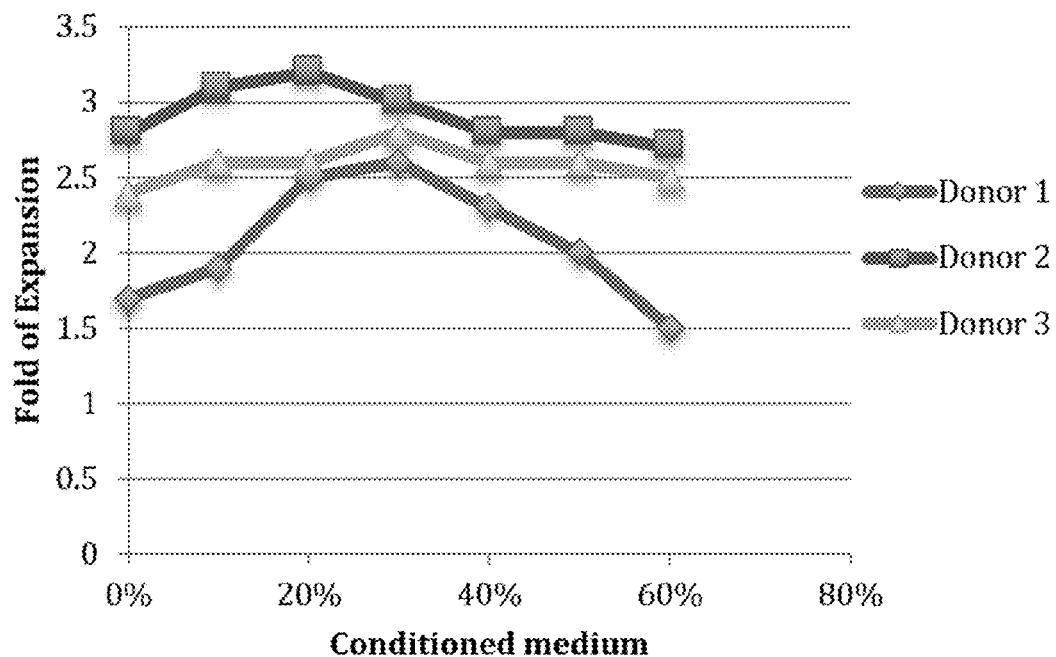
FIG. 2. Graph showing the effect of conditioned media on EBV-specific T cell expansion from cells obtained from three donors, in a Grex-100 bioreactor. Increasing percentages of conditioned media are added to culture media. After one week of co-culture with LCL, the number of expanded T cells is compared to the original number of seeded T cells.

The expected results for T cell expansion are shown in FIG. 2. It is expected that the optimum percentage of conditioned media will be 20-30%, consistent across different donors.

Example 2: Generation of EBV-Transformed LCLs and Expansion of EBV-Specific CTLs Peripheral blood (40-60 mL) obtained from patients with EBV-positive NPC are used to generate both EBV-transformed lymphoblastoid B-cell lines (LCLs) and EBV-specific T cells.

Generation of EBV-Transformed LCLs

Briefly, for LCL generation, $15 \times 10^6$ peripheral blood mononuclear cells (PBMCs) are incubated with concentrated supernatant of B95-8 cultures, in the presence of 1 µg/mL cyclosporin A (Sandoz, Vienna, Austria) to establish an LCL.

LCLs are irradiated at 60 Gy prior to being used for stimulations (on the day of the stimulation).

Expansion of EBV-Specific T Cells

Expansion of EBV-specific T cells by two different methods are compared.

In both methods, a first stimulation is performed as follows:
  $60 \times 10^6$ PBMCs are re-suspended in cell culture media comprising 45% RPMI 1640, 45% Click's media, 10% FBS, 2 mM L-glutamine, and a viable cell count is performed.
  PBMCs are seeded at $2 \times 10^6$ cells/well into wells of a 24 well plate.
  PBMCs are stimulated with irradiated, Acyclovir-treated autologous LCLs at a responder to stimulator ratio of 40:1.
  The cells are cultured for 9-12 days at 37° C. in a 5% $CO_2$ atmosphere.

In both methods, a second stimulation is then performed, as follows:
  Cells are collected at the end of the first stimulation, a viable cell count is performed, and the cells are re-suspended at $1 \times 10^6$ cells/ml in cell culture media comprising 45% RPMI 1640, 45% Click's media, 10% FBS, 2 mM L-glutamine.
  1 ml of cells are added into wells of 24 well plates, or the cell suspension is added into bioreactors at a concentration of $15 \times 10^6$ cells/GRex10, in cell culture media comprising 45% RPMI 1640, 45% Click's media, 10% FBS, 2 mM L-glutamine, and the cells are re-stimulated with autologous irradiated LCLs at a responder to stimulator ratio of 4:1.
  The cells are cultured for 3-4 days, and then the cells are re-suspended in fresh cell culture media comprising 45% RPMI 1640, 45% Click's media, 10% FBS, 2 mM L-glutamine. Recombinant human IL-2 (rhIL-2, Proleukin; Chiron Emeryville, Calif.)) is added to the cell culture at a final concentration of 40-100 IU/ml.

Subsequent Stimulations

Following the second stimulation, cells are collected, a viable cell count is performed. Culture media (i.e. conditioned media) is retained for use in method B below. The cells are then re-suspended at $1 \times 10^6$ cells/ml (in 24 well plate) or $0.5 \times 10^6$ cells/ml (in GRex10) in cell culture media comprising 45% RPMI 1640, 45% Click's media, 10% FBS, 2 mM L-glutamine and re-stimulated with autologous irradiated LCLs at a responder to stimulator ratio of 4:1.

Once $200 \times 10^6$ cells are achieved, cells are then stimulated according to method step A or method step B:

| Method Step A | Method Step B |
| --- | --- |
| $100 \times 10^6$ cells are re-suspended in 200 ml cell culture media comprising 45% RPMI 1640, 45% Click's media, 10% FBS, 2 mM L-glutamine, transferred to GRex 100, and re-stimulated with and the cells are re-stimulated with autologous irradiated LCLs at a responder to stimulator ratio of 4:1, with added rhIL-2 at a final concentration of 40-100 IU/ml. The cells are cultured for 3-4 days at 37° C. in a 5% $CO_2$ atmosphere. | $100 \times 10^6$ cells are re-suspended in: (1) 180 ml cell culture media comprising 45% RPMI 1640, 45% Click's media, 10% FBS, 2 mM L-glutamine, and; (2) 20 ml conditioned media obtained from the culture at the end of the second stimulation (i.e. 10% conditioned media), transferred to GRex 100, and re-stimulated with and the cells are re-stimulated with autologous irradiated LCLs at a responder to stimulator ratio of 4:1, with added rhIL-2 at a final concentration of 40-100 IU/ml. The cells are cultured for 3-4 days at 37° C. in a 5% $CO_2$ atmosphere. |

At the end of a stimulation according to method step A or method step B, cells are collected and re-stimulated according to the same method step A or B.

For re-simulations according to method step B, conditioned media used is from the preceding stimulation according to B.

Example 3: Test of Efficacy

The cytotoxic activity of CTLs expanded by methods including culture in the presence of conditioned media is compared to the cytotoxic activity of CTLs expanded without culture in the presence of conditioned media.

Figure 3:
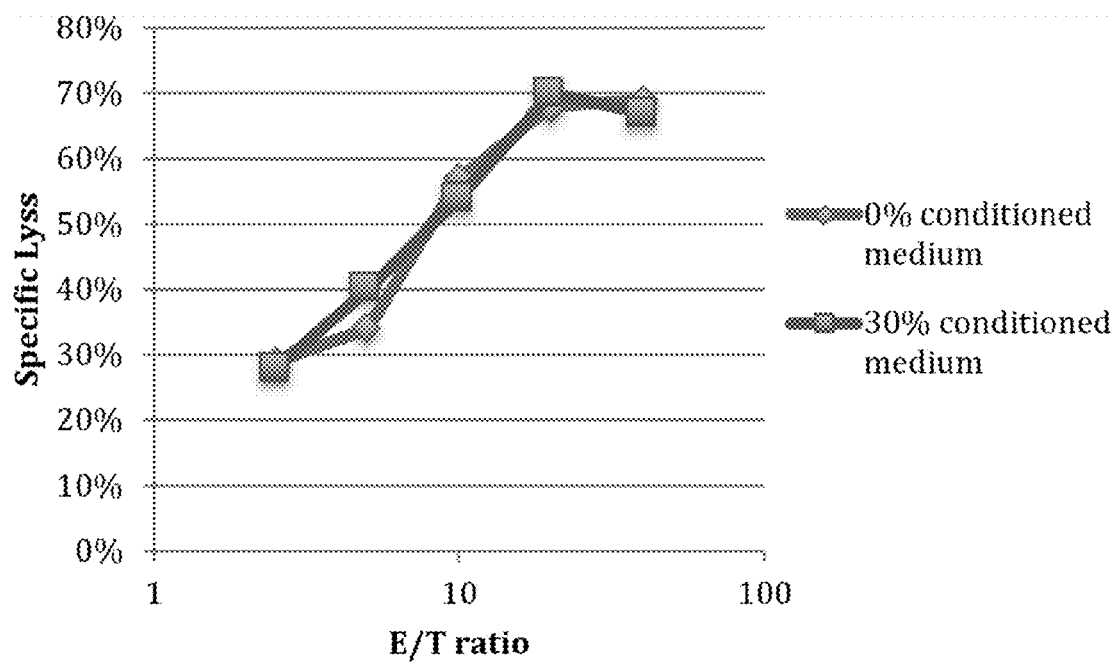
FIG. 3. Graph showing specific killing of EBV-transformed LCL cells by EBV-Specific T cells. T cells expanded by culture in 0% and 30% conditioned medium are co-cultured with LCLs at different effector/target cell ratios, and specific lysis of the LCL cells is measured after 4 hours.

T cells expanded from 0% and 30% conditioned media are added to LCL cells at different Effector/Target cell ratios (E/T ratio), and after 4 hours, specific lysis of the LCL cells is measured. It is expected that there will be very little or no difference between the specific lysis for cells expanded by culture in 0% and 30% conditioned media (FIG. 3).

CTLs expanded at an increased rate are expected to retain the ability to specifically kill EBV-transformed LCL cells.

Example 4: Optimization of Epstein-Barr Virus-Specific T Cells (EB-VSTs) Growth Using Conditioned Medium The following example describes an investigation of the optimal percentage of conditioned media to be included in restimulations for maximum CTL expansion.

Week 1:
Lymphoblastoid cell line (LCL) samples were thawed and cultured for 1 week
Requires minimally $10 \times 10^6$ LCLs to initiate experiment Week 2:
Frozen EB-VST03 cells from different patients were thawed, re-suspended in cell culture media comprising 45% RPMI 1640, 45% Click's media, 10% FBS, 2 mM L-glutamine, and a viable cell count was performed
  EB-VST03 cells were obtained by culture of PMBCs according to Example 2, wherein the PBMCs underwent first and second stimulations, and then a third stimulation according to Method Step A (i.e. in the absence of conditioned media), after which point cells were harvested and frozen
  EB-VST03 cells were seeded at $1 \times 10^6$ cells/well of a 24-well plate
  Cell suspensions were added to bioreactors ($15 \times 10^6$ cells/ G-Rex 10) in cell culture media comprising 45% RPMI 1640, 45% Click's media, 10% FBS, 2 mM L-glutamine, and re-stimulated with autologous irradiated LCLs at a Responder:Stimulator ratio of 4:1.

The cells were cultured for 3-4 days, and then resuspended in cell culture media comprising 45% RPMI 1640, 45% Click's media, 10% FBS and 2 mM L-glutamine.

IL-2 was then added to the cell culture at a final concentration of 40-100 IU/ml.

Week 3 Onwards:

Cells were harvested, pooled, counted and stimulated as described under week 2 above until there were 120×10$^6$ cells.

100×10$^6$ cells were then seeded into G-Rex 100 flasks in cell culture media comprising 45% RPMI 1640, 45% Click's media, 10% FBS, 2 mM L-glutamine, and different percentages of conditioned media (obtained from the culture at the end of the preceding stimulation culture), as follows:

| Cell culture media comprising 45% RPMI 1640, 45% Click's media, 10% FBS, 2 mM L-glutamine | Conditioned media | % Conditioned media |
|---|---|---|
| 200 ml | 0 ml | 0% |
| 170 ml | 30 ml | 15% |
| 140 ml | 60 ml | 30% |
| 110 ml | 90 ml | 45% |

The cells were then cultured for 3-4 days at 37° C. in a 5% $CO_2$ atmosphere.

IL-2 was then added to the cell culture at a final concentration of 40-100 IU/ml.

After one week, the cells were harvested and a viable cell count was performed.

Figure 4:
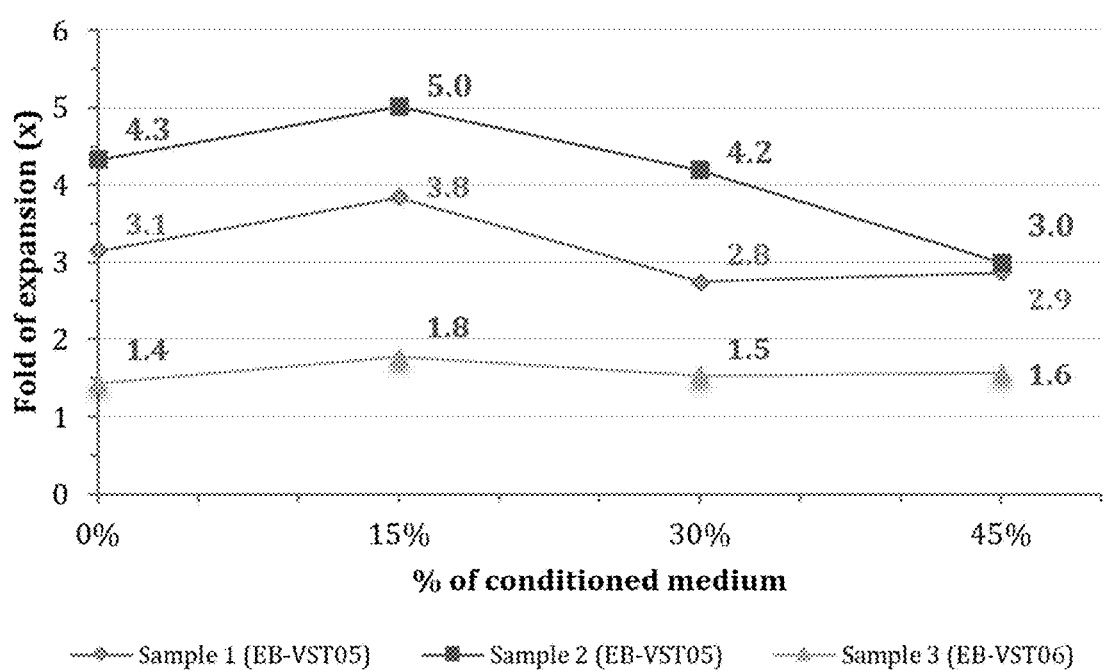
FIG. 4. Graph showing the effect of the presence of different percentages of conditioned media on fold expansion of EBV-specific CTLs, cultured in Grex-100 bioreactor culture vessels.

All viabilities were observed to be greater than 70%. The results are shown in FIG. 4.

It was found that culture in cell culture media comprising 45% RPMI 1640, 45% Click's media, 10% FBS, 2 mM L-glutamine and up to 15% conditioned media gave the highest yield of EB-VSTs, which was ~20% higher than the rate of EB-VST as compared to using 100% of cell culture media comprising 45% RPMI 1640, 45% Click's media, 10% FBS, 2 mM L-glutamine.

Fold expansion of EB-VSTs decreased when higher percentages (i.e. 30%, 45%) of conditioned media were used.

Fold expansion observed for Sample 3—EB-VST was not as pronounced as observed for Sample 1 & Sample 2. This might be because Sample 3 EBV-VST underwent an additional cycle of stimulation, with the result that cell growth was overstressed.

It is concluded that a combination of 15% conditioned media with 85% fresh culture media (complete Click's medium) produced highest EB-VST yield i.e. higher EB-VST expansion rate as compared to using 100% fresh culture media.

Whilst the effect of conditioned medium on EB-VST growth varies among different individuals, it was observed that in every case, using 15% conditioned medium gave the best expansion rate.

The invention claimed is:

1. A method of treating a cancer in a subject, the method comprising:
   (1) isolating T cells from a subject;
   (2) generating or expanding a population of T cells specific for Epstein-Barr Virus (EBV) by a method comprising: stimulating T cells by culture in the presence of antigen presenting cells (APCs) presenting a peptide of EBV, wherein 12.5% to 17.5% of the media in which the cells are cultured is cell-free conditioned media obtained from a separate stimulation culture comprising T cells and APCs presenting a peptide of EBV; and
   (3) administering the generated or expanded population of T cells to a subject, wherein the cancer is an EBV-positive cancer.

2. The method according to claim 1, wherein the cell-free conditioned media is obtained from a separate stimulation culture comprising T cells (responders) and APCs presenting a peptide of EBV (stimulators) at a responder:stimulator ratio of 2:1 to 7:1 for a period of 1 to 8 days.

3. The method according to claim 1, wherein stimulating T cells (responders) by culture in the presence of APCs presenting a peptide of EBV (stimulators) comprises culture in the presence of EBV-transformed lymphoblastoid cell lines (LCLs) at a responder to stimulator ratio of 2:1 to 7:1 for a period of 1 to 8 days, in media comprising:
   (a) cell culture media comprising 40-50% RPMI-1640 medium, 40-50% Click's medium, 5-20% fetal bovine serum (FBS), and 1-5 mM L-glutamine,
   (b) 12.5% to 17.5% cell free conditioned media obtained by a method comprising: stimulating T cells by culture in the presence of EBV-transformed LCLs at a responder to stimulator ratio of 2:1 to 7:1 in cell culture media comprising 40-50% RPMI-1640 medium, 40-50% Click's medium, 5-20% FBS, and 1-5 mM L-glutamine, and added IL-2 at a final concentration of 10-200 IU/ml, for a period of 1 to 8 days, and
   (c) added IL-2 at a final concentration of 10-200 IU/ml.

4. The method according to claim 1, wherein the APCs presenting a peptide of EBV are EBV-transformed lymphoblastoid cell line (LCL) cells.

5. The method according to claim 1, wherein the cancer is EBV-positive nasopharyngeal carcinoma (NPC).

6. The method according to claim 1, wherein about 15% of the media in which the cells are cultured is cell-free conditioned media.

7. The method according to claim 1, wherein step (2) additionally comprises:
   collecting the generated or expanded population of T cells.

8. A method of treating a cancer in a subject, the method comprising:
   (1) isolating T cells from a subject;
   (2) generating or expanding a population of T cells specific for Epstein-Barr Virus (EBV) by a method comprising: stimulating T cells by culture in the presence of antigen presenting cells (APCs) presenting a peptide of EBV, wherein 12.5% to 17.5% of the media in which the cells are cultured is cell-free conditioned media, wherein the cell-free conditioned media is obtained from a separate stimulation culture comprising T cells (responders) and APCs presenting a peptide of EBV (stimulators) at a responder:stimulator ratio of 2:1 to 7:1 for a period of 1 to 8 days; and
   (3) administering the generated or expanded population of T cells to a subject, wherein the cancer is an EBV-positive cancer.

9. The method according to claim 8, wherein stimulating T cells (responders) by culture in the presence of APCs presenting a peptide of EBV (stimulators) comprises culture in the presence of EBV-transformed lymphoblastoid cell lines (LCLs) at a responder to stimulator ratio of 2:1 to 7:1 for a period of 1 to 8 days, in media comprising:

(a) cell culture media comprising 40-50% RPMI-1640 medium, 40-50% Click's medium, 5-20% fetal bovine serum (FBS), and 1-5 mM L-glutamine, (b) 12.5% to 17.5% cell-free conditioned media obtained by a method comprising: stimulating T cells by culture in the presence of EBV-transformed LCLs at a responder to stimulator ratio of 2:1 to 7:1 in cell culture media comprising 40-50% RPMI-1640 medium, 40-50% Click's medium, 5-20% FBS, and 1-5 mM L-glutamine, and added IL-2 at a final concentration of 10-200 IU/ml, for a period of 1 to 8 days, and (c) added IL-2 at a final concentration of 10-200 IU/ml.

10. The method according to claim 8, wherein the cancer is EBV-positive nasopharyngeal carcinoma (NPC).

11. The method according to claim 8, wherein the 12.5% to 17.5% cell-free conditioned media is about 15% cell-free conditioned media.

12. The method according to claim 8, wherein step (2) additionally comprises:
collecting the generated or expanded population of T cells.

13. A method for generating or expanding a population of T cells specific for Epstein-Barr Virus (EBV), comprising stimulating T cells by culture in the presence of antigen presenting cells (APCs) presenting a peptide of EBV, wherein 12.5% to 17.5% of the media in which the cells are cultured is cell-free conditioned media obtained from a separate stimulation culture comprising T cells and APCs presenting a peptide of EBV.

14. The method according to claim 13, wherein the cell-free conditioned media is obtained from a separate stimulation culture comprising T cells (responders) and APCs presenting a peptide of EBV (stimulators) at a responder:stimulator ratio of 2:1 to 7:1 for a period of 1 to 8 days.

15. The method according to claim 13, wherein stimulating T cells (responders) by culture in the presence of APCs presenting a peptide of EBV (stimulators) comprises culture in the presence of EBV-transformed lymphoblastoid cell lines (LCLs) at a responder to stimulator ratio of 2:1 to 7:1 for a period of 1 to 8 days, in media comprising:

(a) cell culture media comprising 40-50% RPMI-1640 medium, 40-50% Click's medium, 5-20% fetal bovine serum (FBS), and 1-5 mM L-glutamine, (b) 12.5% to 17.5% cell-free conditioned media obtained by a method comprising: stimulating T cells by culture in the presence of EBV-transformed LCLs at a responder to stimulator ratio of 2:1 to 7:1 in cell culture media comprising 40-50% RPMI-1640 medium, 40-50% Click's medium, 5-20% FBS, and 1-5 mM L-glutamine, and added IL-2 at a final concentration of 10-200 IU/ml, for a period of 1 to 8 days, and (c) added IL-2 at a final concentration of 10-200 IU/ml.

16. The method according to claim 13, wherein the APCs presenting a peptide of EBV are EBV-transformed lymphoblastoid cell line (LCL) cells.

17. The method according to claim 13, wherein the 12.5% to 17.5% of cell-free conditioned media is about 15% of cell-free conditioned media.

18. The method according to claim 13, wherein step (2) additionally comprises:
collecting the generated or expanded population of T cells.

* * * * *